United States Patent
Delcanale et al.

(10) Patent No.: US 8,383,826 B2
(45) Date of Patent: Feb. 26, 2013

(54) DERIVATIVES OF 1-PHENYL-2-PYRIDINYL ALKYL ALCOHOLS AS PHOSPHODIESTERASE INHIBITORS

(75) Inventors: Maurizio Delcanale, Parma (IT); Elisabetta Armani, Parma (IT); Gabriele Amari, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/354,896

(22) Filed: Jan. 20, 2012

(65) Prior Publication Data

US 2012/0116091 A1    May 10, 2012

Related U.S. Application Data

(60) Division of application No. 13/032,288, filed on Feb. 22, 2011, now abandoned, which is a continuation of application No. 12/188,631, filed on Aug. 8, 2008, now Pat. No. 7,923,565.

(30) Foreign Application Priority Data

Aug. 8, 2007   (EP) .................................... 07114019

(51) Int. Cl.
 *A61K 31/44*   (2006.01)
 *C07D 213/62*   (2006.01)
(52) U.S. Cl. ........................................ 546/301; 514/345
(58) Field of Classification Search ........................ None
  See application file for complete search history.

(56) References Cited

U.S. PATENT DOCUMENTS

| | | | |
|---|---|---|---|
| 7,671,066 B2 | 3/2010 | Amari et al. | |
| 7,820,698 B2 | 10/2010 | Rizzi et al. | |
| 7,923,565 B2 | 4/2011 | Delcanale et al. | |
| 7,968,724 B2 | 6/2011 | Armani et al. | |
| 8,203,000 B2 | 6/2012 | Delcanale et al. | |
| 2006/0239927 A1 | 10/2006 | Ohshima et al. | |
| 2008/0015226 A1 | 1/2008 | Amari et al. | |
| 2010/0204256 A1 | 8/2010 | Amari et al. | |
| 2011/0144070 A1 | 6/2011 | Delcanale et al. | |
| 2011/0144075 A1 | 6/2011 | Delcanale et al. | |
| 2012/0031403 A1 | 2/2012 | Cocconi et al. | |
| 2012/0034172 A1 | 2/2012 | Bonelli et al. | |

FOREIGN PATENT DOCUMENTS

| | | |
|---|---|---|
| EP | 1 634 606 | 3/2006 |
| WO | WO 9402465 A1 * | 2/1994 |

OTHER PUBLICATIONS

CAPLUS 1995 752754.*
Darrow, Jonathan, "The Patentability of Enantiomers: Implications for the Pharmaceutical Industry", 2007 Stan. Tech. L. Rev. 2, Feb. 27, 2007.
Ducharme et. al., "Substituted 2-pyridinemethanol derivatives as potent and selective phosphodiesterase-4 inhibitors", Bioorganic & Medicinal Chemistry Letters 2003, 13 (11), pp. 1923-1926.
Patani et al., "Bioisosterism: A Rational Approach in Drug Design", Chem. Rev. 1996, 96, pp. 3147-3176.
Huang, Z. et al., Current Op. Chem. Biol. 2001, vol. 5, pp. 432-438.
Zhang, K, et al., Expert Op. Ther. Targets 2005 vol. 9, pp. 1283-1305.
Patani, G. et al., Chem. Rev. 1996, vol. 96, pp. 3147-3176.
U.S. Appl. No. 13/488,818, filed Jan. 5, 2012, Armani, et al.

* cited by examiner

*Primary Examiner* — Janet Andres
*Assistant Examiner* — Heidi Reese
(74) *Attorney, Agent, or Firm* — Oblon, Spivak, McClelland, Maier & Neustadt, L.L.P.

(57) ABSTRACT

Derivatives of 1-phenyl-2-pyridinyl alkyl alcohols are useful as inhibitors of the phosphodiesterase 4 (PDE4) enzyme.

6 Claims, No Drawings

DERIVATIVES OF 1-PHENYL-2-PYRIDINYL ALKYL ALCOHOLS AS PHOSPHODIESTERASE INHIBITORS

CROSS REFERENCES TO RELATED APPLICATIONS

This application is a Divisional Application of U.S. patent application Ser. No. 13/032,288, filed on Feb. 22, 2011, which was a continuation of U.S. patent application Ser. No. 12/188,631, filed on Aug. 8, 2008, now U.S. Pat. No. 7,923,565, and claims priority to European Patent Application No. 07114019.8, filed on Aug. 8, 2007, which is incorporated herein by reference in its entirety.

BACKGROUND OF THE INVENTION

1. Field of the Invention

The present invention relates to inhibitors of the phosphodiesterase 4 (PDE4) enzyme. More particularly, the invention relates to compounds that are derivatives of 1-phenyl-2-pyridinyl alkyl alcohols, methods of preparing such compounds, compositions containing them, and therapeutic use thereof.

2. Discussion of the Background

Airway obstruction characterizes a number of severe respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, avoiding any systemic side-effects, thus resulting in a more rapid clinical response and a higher therapeutic ratio.

Inhaled corticosteroids are the current maintenance therapy of choice for asthma and together with bronchodilator $beta_2$-agonists for acute symptom relief, they form the mainstay of current therapy for the disease. The current management of COPD is largely symptomatic by means of bronchodilating therapy with inhaled anticholinergics and inhaled $beta_2$-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (see, Jacobitz, S. et al., *Mol. Pharmacol.*, vol. 50, pp. 891-899 (1996)), which is found in the immune and inflammatory cells. While both forms appear to exhibit catalytic activity, they differ with respect to their sensitivity to inhibitors. In particular compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as cilomilast and roflumilast. However, even these compounds are not provided with a good selectivity towards LPDE4.

Other classes of compounds acting as PDE4 inhibitors have been disclosed in the prior art. For example, EP 1 634 606 discloses, among others, ketone derivatives like benzofuran or 1,3-benzodioxole derivatives.

WO 9402465 discloses, among others, ketone derivatives of general formula

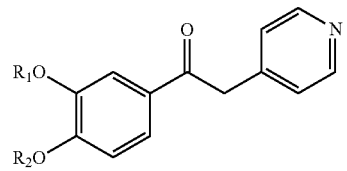

wherein $R_1$ is lower alkyl and $R_2$ may be alkyl, alkenyl, cycloalkyl, cycloalkyl, cycloalkenyl, cyclothioalkyl or cyclothioalkenyl. WO 9535281 in the name of Celltech Therapeutics concerns tri-substituted phenyl derivatives. Both applications are silent about the problems of the side effects associated with inhibition of HPDE4 and do not report data regarding affinity toward HPDE4 and LPDE4.

Therefore, although several PDE4 inhibitors have been disclosed so far, there is still a need for more efficacious and better tolerated compounds.

In particular, it would be highly advantageous to provide more selective compounds, e.g. endowed with a higher affinity toward the LPDE4 with respect to the affinity to HPDE4, in order to attenuate or avoid the side effects associated with its inhibition.

SUMMARY OF THE INVENTION

Accordingly, it is one object of the present invention to provide novel compounds which are useful as phosphodiesterase 4 (PDE4) inhibitors.

It is another object of the present invention to provide novel compounds which are useful as PDE4 inhibitors with an improved selectivity toward LPDE4.

It is another object of the present invention to provide novel compounds which are useful for the prevention and/or treatment of any disease characterized by PDE4 overactivity and/or wherein an inhibition of PDE4 activity is desirable.

It is another object of the present invention to provide novel compounds which are useful for the prevention and/or treatment of a disease the respiratory tract characterized by airway obstruction such as asthma and COPD.

It is another object of the present invention to provide novel methods of making such a compound.

It is another object of the present invention to provide novel pharmaceutical compositions which contain such a compound.

It is another object of the present invention to provide novel methods for the prevention and/or treatment of any disease characterized by phosphodiesterase 4 (PDE4) overactivity and/or wherein an inhibition of PDE4 activity is desirable.

It is another object of the present invention to provide novel methods for the prevention and/or treatment of a disease the respiratory tract characterized by airway obstruction such as asthma and COPD.

The invention is provides compounds which act as inhibitors of the phosphodiesterase 4 (PDE4) enzyme, methods of preparing said compounds, compositions containing them and therapeutic use thereof.

The present invention addresses these issues by providing PDE4 inhibitors having an improved selectivity toward LPDE4.

As a matter of fact, it has now been found that providing a PDE4 inhibitor with an additional moiety interacting with the active site of the PDE4, there is an improvement in the selectivity of the inhibitors towards LPDE4.

The PDE4 inhibitors of the present invention efficaciously act upon inhalation administration and could be characterized by a good persistency in the lung and a short systemic duration.

In particular the invention is directed to derivatives of 1-phenyl-2-pyridinyl alkyl alcohols of general formula (I):

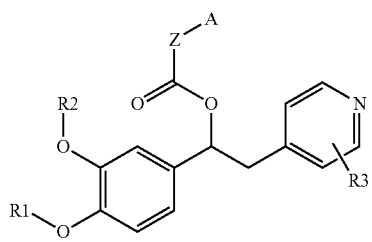

(I)

wherein:
Z is selected from the group consisting of
$(CH_2)_m$ wherein m=0, 1 or 2;
$(CH_2)_nO$ wherein n=1, 2 or 3;
$O(CH_2)_p$ wherein p=0, 1, 2 or 3;
$CH_2SO_2$;
$CHNR_6$;
$CH_2NR_6$;
$NR_6$ wherein $R_6$ is H or a linear or branched $(C_1-C_4)$ alkyl;
$OCOR_4R_5$; and
$CR_4R_5$ wherein
$R_4$ is independently selected from H or a linear or branched $(C_1-C_4)$ alkyl, preferably methyl, optionally substituted by a $(C_1-C_4)$ cycloalkyl, and
$R_5$ is independently selected from the group consisting of
linear or branched $(C_1-C_4)$ alkyl, preferably methyl;
phenyl;
benzyl;
$NH_2$; and
HNCOOR', wherein R' is linear or branched $(C_1-C_4)$ alkyl,
preferably t-butyl;
$R_1$ and $R_2$ are different or the same and are independently selected from the group consisting of:
H;
linear or branched $(C_1-C_6)$ alkyl, optionally substituted by one or more substituents selected from $(C_3-C_7)$ cycloalkyl or $(C_5-C_7)$ cycloalkenyl;
$(C_3-C_7)$ cycloalkyl;
$(C_5-C_7)$ cycloalkenyl; linear or branched $(C_2-C_6)$ alkenyl; and
linear or branched $(C_2-C_6)$ alkynyl;
$R_3$ is one or more substituents independently selected from the group consisting of H, CN, $NO_2$, $CF_3$ and halogen atoms;
A is a ring system, that is a mono- or bicyclic ring which may be saturated, partially unsaturated or unsaturated, such as aryl, $(C_3-C_8)$ cycloalkyl or heteroaryl, said ring system A having 5 to 10 ring atoms in which at least one ring atom is a heteroatom (e.g. N, S or O), in which the optional substituent $R_x$ on the A ring system may be one or more, may be the same or different, and is independently selected from the group consisting of:
linear or branched $(C_1-C_6)$ alkyl optionally substituted by one or more $(C_3-C_7)$ cycloalkyl;
linear or branched $(C_2-C_6)$ alkenyl optionally substituted by one or more $(C_3-C_7)$ cycloalkyl;
linear or branched $(C_2-C_6)$ alkynyl optionally substituted by one or more $(C_3-C_7)$ cycloalkyl;
$(C_5-C_7)$ cycloalkenyl;
phenyl;
$(C_3-C_7)$ heterocycloalkyl; and
$OR_7$ wherein $R_7$ is selected from the group consisting of:
H;
$(C_1-C_{10})$ alkyl optionally substituted by one or more $(C_3-C_7)$ cycloalkyl;
$(C_3-C_7)$ cycloalkyl;
$(C_1-C_4)$ alkylene-$(C_3-C_7)$ heterocycloalkyl;
$CO(C_1-C_6)$ alkyl;
$COO(C_1-C_6)$ alkyl;
phenyl;
benzyl;
$(C_1-C_{10})$ alkylene-$NR_8R_9$ wherein $R_8$ and $R_9$ are independently selected from the group consisting of H, linear or branched $(C_1-C_6)$ alkyl and they form with the nitrogen atom to which they are linked a saturated, partially saturated or unsaturated ring, preferably $NR_8R_9$ is linked to $(C_1-C_{10})$ alkyl forming for example saturated, partially saturated or unsaturated piperidine, oxazine, imidazole rings, wherein these rings are optionally substituted by $(C_1-C_4)$ alkyl; and
halogen atoms;
CN;
$NO_2$;
$NR_{10}R_{11}$, wherein $R_{10}$ and $R_{11}$ are different or the same and are independently selected from the group consisting of:
H;
linear or branched $(C_1-C_6)$ alkyl, optionally substituted with phenyl or $(C_3-C_7)$ cycloalkyl;
$COC_6H_5$;
CO—$(C_1-C_4)$ alkyl;
COO—$(C_1-C_4)$ alkyl;
CONH—$(C_1-C_6)$ alkylene-$R_{12}$, wherein $R_{12}$ is selected from the group consisting of:
H;
$(C_1-C_4)$ alkyl; and
$OR_4R_5$; and
$CONH(C_1-C_4)$ alkylene-$N(C_1-C_4)$ alkyl;
or they form with the nitrogen atom to which they are linked a saturated or partially saturated ring, preferably a piperidyl ring;
$(C_1-C_4)$ alkylene-$NR_{10}R_{11}$;
$COR_{12}$ wherein $R_{12}$ is phenyl or linear or branched $(C_1-C_6)$ alkyl;
oxo;
$HNSO_2R_{13}$ wherein $R_{13}$ is $(C_1-C_4)$ alkyl or a phenyl optionally substituted with halogen atoms or with a $(C_1-C_4)$ alkyl group;
$SO_2R_{14}$ wherein $R_{14}$ is $(C_1-C_4)$ alkyl, OH or $NR_{10}R_{11}$ wherein $R_{10}$ and $R_{11}$ are as defined above;
$SOR_{15}$ wherein $R_{15}$ is phenyl or $(C_1-C_4)$ alkyl;
$SR_{16}$ wherein $R_{16}$ is H, phenyl or $(C_1-C_4)$ alkyl;
$COOR_{17}$ wherein $R^{17}$ is H, $(C_1-C_4)$ alkyl, phenyl or benzyl; and
$(CH_2)_qOR_{18}$, wherein q=1, 2, 3 or 4 and $R_{18}$ is H or $(C_1-C_4)$ cycloalkyl.
and pharmaceutically acceptable salts and N-oxides on the pyridine ring thereof.

The invention also provides the pharmaceutically acceptable salts and/or solvates thereof.

The invention further involves the corresponding N-oxides on the pyridine ring.

The invention further comprises a process for the preparation of compounds of general formula (I).

The present invention also provides pharmaceutical compositions which contain a compound of general formula (I) alone or in combination with in admixture with one or more pharmaceutically acceptable carriers.

In a further aspect the present invention provides the use of the compounds of general formula (I) as a medicament.

In a further aspect the present invention provides the use of the compounds of general formula (I) for the manufacture of a medicament.

In particular, the present invention provides methods for the prevention and/or treatment of any disease characterized by phosphodiesterase 4 (PDE4) overactivity and/or wherein an inhibition of PDE4 activity is desirable by administering a compound of formula (I) or a salt or N-oxide thereof.

In particular the compounds of general formula (I) alone or combined with other active ingredients may be administered for the prevention and/or treatment of a disease the respiratory tract characterized by airway obstruction such as asthma and COPD.

In a further aspect the present invention provides the use of compounds of general formula (I) for the preparation of a medicament for the prevention and/or treatment of an inflammatory disease, disorder or condition characterized by or associated with an undesirable inflammatory immune response or induced by or associated with an excessive secretion of TNF-α and PDE4.

Moreover the present invention provides a method for prevention and/or treatment of any disease wherein PDE4 inhibition is required, said method comprises administering to a patient in need of such treatment a therapeutically effective amount of a compound of general formula (I).

DETAILED DESCRIPTION OF THE PREFERRED EMBODIMENTS

In the context of the present invention, the term "halogen atoms" as used herein includes fluorine, chlorine, bromine, and iodine, preferably chlorine.

As used herein, the expression "linear or branched ($C_1$-$C_x$) alkyl" where x is an integer greater than 1, refers to straight-chained and branched alkyl groups wherein the number of constituent carbon atoms is in the range 1 to x. Particular alkyl groups are methyl, ethyl, n-propyl, isopropyl and t-butyl. Optionally in said groups one or more hydrogen atoms can be replaced by halogen atoms, preferably chlorine or fluorine.

The derived expressions "($C_2$-$C_6$) alkenyl" and "($C_2$-$C_6$) alkynyl", are to be construed in an analogous manner.

As used herein, the expression "($C_3$-$C_x$) cycloalkyl", where x is an integer greater than 3, refers to cyclic non-aromatic hydrocarbon groups containing from 3 to x ring carbon atoms. Examples include cyclopropyl, cyclobutyl, cyclopentyl, cyclohexyl and cycloheptyl. Optionally in said groups one or more hydrogen atoms can be replaced by halogen atoms, preferably chlorine or fluorine.

As used herein, the expression "($C_3$-$C_7$) heterocycloalkyl", refers to cyclic non-aromatic hydrocarbon groups containing one or more heteroatoms (e.g. N, S or O), optionally substituted by one or more ($C_1$-$C_4$) alkyl.

The derived expressions "($C_1$-$C_x$) cycloalkoxyl" is to be construed in an analogous manner.

The derived expression "($C_5$-$C_x$) cycloalkenyl", where x is an integer greater than 5, is to be construed in an analogous manner.

As used herein, the expression "ring system" refers to mono- or bicyclic ring systems which may be saturated, partially unsaturated or unsaturated, such as aryl, ($C_3$-$C_8$) cycloalkyl or heteroaryl, having 5 to 10 ring atoms in which at least one ring atom is a hereoatom (e.g. N, S or O). Examples of suitable monocyclic systems include phenyl, pyridyl, piperazinyl, piperidinyl, morpholinyl, cyclopentyl, cyclohexyl, cyclohexenyl, cycloheptyl, dioxane, imidazole and imidazolidine.

Examples of suitable bicyclic systems include naphthyl, quinolinyl, isoquinolinyl, indenyl, fluorene, benzimidazole, benzimidazolidine, xanthine and the partially- or fully-hydrogenated derivatives thereof.

The invention provides a class of compounds acting as inhibitors of the phosphodiesterase 4 (PDE4) enzyme. Said class of compounds inhibits the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3 and tumor necrosis factor-alpha (TNF-α).

It also leads to an airway smooth muscle relaxation and a decrease in oedema.

The catalytic site of PDE4 has been previously identified: it mainly comprises a hydrophobic region in which two sub-pockets are present, e.g. $S_0$ and $S_1$, and a hydrophilic region containing the metal ions $Zn^{2+}$ and $Mg^{2+}$, that in turn comprises the sub-pocket $S_2$ spreading around the metal ions and a sub-pocket $S_3$ which branches approximately 90° from the middle of the hydrophobic pocket.

Most of the compounds of the prior art are provided with a moiety able of interacting with the sub-pockets $S_0$ and $S_1$ of the hydrophobic region such as a substituted cathecol group and with another moiety able of indirectly interacting with the metal ions of the $S_2$ sub-pocket, for example a heterocycle such as pyridine or pyrrolidone.

The present invention is directed to compounds which were designed so that they could maintain the interactions with the sub-pockets $S_0$ and $S_1$ by means of the substituted catecol moiety and the interaction with the metal ions region by means of the pyridine ring like other known PDE4 inhibitors but differ for the presence of a further group able of establishing an additional interaction with the sub-pocket $S_3$.

In particular the present invention relates to derivatives of 1-phenyl-2-pyridinyl alkyl alcohols of general formula (I)

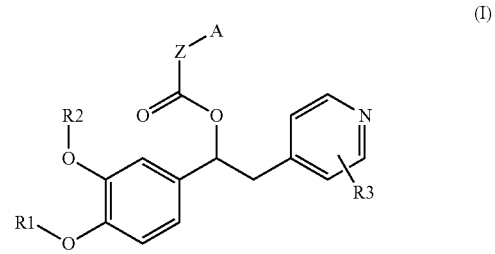

(I)

Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid.

It will be apparent to those skilled in the art that the compounds of general formula (I) may contain asymmetric centers. Therefore the invention also includes the optical stereoisomers and mixtures thereof.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The compounds of general formula (I) were found to show an in vitro inhibitory activity toward the PDE4 enzyme in the nM range and they turned out to be endowed of a good activity in the lungs upon intra-tracheal administration in an animal model of COPD. They also exhibited in some cases sustained pulmonary levels in the lungs, while no detectable plasmatic levels were found which is an index of a short systemic action.

One possible explanation for the unexpectedly high selectivity of these compounds for LPDE4 in comparison to HPDE4 is that they all feature a moiety which could fit into the $S_3$ sub-pocket of the catalytic site of the PDE4 enzyme through the A substituent.

As it can be appreciated from the results reported in the Example 13, a compound representative of the invention was indeed found about 1319-fold more selective toward LPDE4 versus HPDE4.

A preferred group of compounds of general formula (I) is that wherein the 2-pyridinyl ring is substituted in 3 and 5 with two atoms of chlorine, according to the general formula (II)

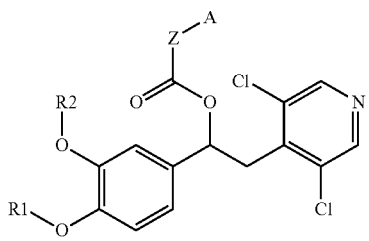

(II)

wherein $R_1$, $R_2$, Z and A are as defined above.

Advantageously when $R_1$ or $R_2$ is H, the other substituent on the cathecol group is different from H.

Preferably $R_1$ and $R_2$ are both different from H.

A first group of more preferred compounds of general formula (II) is that in which:

$R_1$ and $R_2$ are as defined above;

Z is $(CH)_n$ wherein n is 0; and

A is as defined above.

A second group of more preferred compounds is that in which:

$R_1$ and $R_2$ are as defined above;

Z is $CHR_5$ wherein $R_5$ is linear or branched $(C_1-C_4)$ alkyl, preferably methyl; and A is as defined above.

A third group of more preferred compounds is that in which:

$R_1$ and $R_2$ are as defined above;

Z is $CR_4R_5$ wherein $R_4$ and $R_5$ are both linear or branched $(C_1-C_4)$ alkyl and they form a ring together with the carbon atom to which they are linked having 3, 4, 5 or 6 carbon atoms, preferably having 3 carbon atoms; and A is as defined above.

In one of the preferred embodiments, A is substituted with Rx, and Rx is selected from the group consisting of linear or branched $(C_1-C_6)$ alkyl, linear or branched $(C_2-C_6)$ alkenyl, linear or branched $(C_2-C_6)$ alkynyl or $OR_7$ wherein $R_7$ is as defined above.

In another preferred embodiment A is substituted with Rx, and $R_x$ is a group capable of improving the aqueous solubility of the whole molecule such as $NR_{10}R_{11}$ or $HNSO_2R_{13}$ wherein $R_{10}$, $R_{11}$ and $R_{13}$ are as defined above.

In a particular embodiment of the invention, when A is a heteroaryl ring, the ring is preferably selected from the group consisting of pyrrole, pyrazole, furan, thiophene, imidazole, oxazole, isoxazole, thiazole, pyridine, pyrimidine, pyrazine and pyran, imidazole, imidazolidine and more preferably pyridine.

According to a preferred embodiment the present invention provides the compounds reported below:

| Compound | Chemical name |
|---|---|
| 1 | 2-(4-isobutyl-phenyl)-propionic acid 2-(3,5-dichloro-pyridin-4-yl)-1-(3,4-dimethoxy-phenyl)-ethyl ester |
| 2 | phenyl-acetic acid 2-(3,5-dichloro-pyridin-4-yl)-1-(3,4-dimethoxy-phenyl)-ethyl ester |
| 3 | 1-phenyl-cyclopropanecarboxylic acid 2-(3,5-dichloro-pyridin-4-yl)-1-(3,4-dimethoxy-phenyl)-ethyl ester |
| 4 | 3,4-dimethoxy-benzoic acid 2-(3,5-dichloro-pyridin-4-yl)-1-(3,4-dimethoxy-phenyl)-ethyl ester |
| 5 | (S)-tert-butoxycarbonylamino-phenyl-acetic acid 1-(3-cyclopropylmethoxy-4-difluoromethoxy-phenyl)-2-(3,5-dichloro-pyridin-4-yl)-ethyl ester |
| 6 | (R)-tert-butoxycarbonylamino-phenyl-acetic acid 1-(3-cyclopropylmethoxy-4-difluoromethoxy-phenyl)-2-(3,5-dichloro-pyridin-4-yl)-ethyl ester |
| 7 | (S)-amino-phenyl-acetic acid 1-(3-cyclopropylmethoxy-4-difluoromethoxy-phenyl)-2-(3,5-dichloro-pyridin-4-yl)-ethyl ester |
| 8 | (R)-amino-phenyl-acetic acid 1-(3-cyclopropylmethoxy-4-difluoromethoxy-phenyl)-2-(3,5-dichloro-pyridin-4-yl)-ethyl ester |
| 9 | 2-(4-isobutyl-phenyl)-propionic acid 1-(3-cyclopentyloxy-4-methoxy-phenyl)-2-(3,5-dichloro-pyridin-4-yl)-ethyl ester |

-continued

| Compound | Chemical name |
|---|---|
| 11 | 3-cyclopropylmethoxy-4-difluoromethoxy-benzoic acid 1-(3-cyclopropylmethoxy-4-difluoromethoxy-phenyl)-2-(3,5-dichloro-pyridin-4-yl)-ethyl ester |
| 12 | 2-(4-isobutyl-phenyl)-propionic acid 1-(3-cyclopropylmethoxy-4-difluoromethoxy-phenyl)-2-(3,5-dichloro-pyridin-4-yl)-ethyl ester |
| 13 | 2-(4-isobutyl-phenyl)-propionic acid 2-(3,5-dichloro-1-oxy-pyridin-4-yl)-1-(3,4-dimethoxy-phenyl)-ethyl ester |
| 14 | 3-cyclopropylmethoxy-4-difluoromethoxy-benzoic acid 1-(3-cyclopropylmethoxy-4-difluoromethoxy-phenyl)-2-(3,5-dichloro-1-oxy-pyridin-4-yl)-ethyl ester |
| 15 | 2-(4-isobutyl-phenyl)-propionic acid 1-(3-cyclopropylmethoxy-4-difluoromethoxy-phenyl)-2-(3,5-dichloro-1-oxy-pyridin-4-yl)-ethyl ester |
| 16 | 2-(4-amino-phenyl)-propionic acid 2-(3,5-dichloro-pyridin-4-yl)-1-(3,4-dimethoxy-phenyl)-ethyl ester |
| 17 | 2-(4-methanesulfonylamino-phenyl)-propionic acid 2-(3,5-dichloro-pyridin-4-yl)-1-(3,4-dimethoxy-phenyl)-ethyl ester |
| 25 | 4-(2-piperidin-1-yl-ethoxy)-benzoic acid 1-(3-cyclopropylmethoxy-4-difluoromethoxy-phenyl)-2-(3,5-dichloro-1-oxy-pyridin-4-yl)-ethyl ester |
| 26 | 3-cyclopropylmethoxy-4-difluoromethoxy-benzoic acid 1-(3-cyclopentyloxy-4-methoxy-phenyl)-2-(3,5-dichloro-1-oxy-pyridin-4-yl)-ethyl ester |
| 27 | 4-(2-piperidin-1-yl-ethoxy)-benzoicacid 2-(3,5-dichloro-1-oxy-pyridin-4-yl)-1-(3,4-dimethoxy-phenyl)-ethyl ester |
| 28 | isonicotinic acid 1-(3-cyclopropylmethoxy-4-difluoromethoxy-phenyl)-2-(3,5-dichloro-1-oxy-pyridin-4-yl)-ethyl ester |
| 29 | nicotinic acid 1-(3-cyclopropylmethoxy-4-difluoromethoxy-phenyl)-2-(3,5-dichloro-1-oxy-pyridin-4-yl)-ethyl ester |
| 30 | 4-(2-imidazol-1-yl-ethoxy)-benzoic acid 1-cyclopropylmethoxy-4-difluoromethoxy-phenyl)-2-(3,5-dichloro-1-oxy-pyridin-4-yl)-ethyl ester |
| 31 | 1-(2-{4-[1-(3-cyclopropylmethoxy-4-difluoromethoxy-phenyl)-2-(3,5-dichloro-1-oxy-pyridin-4-yl)-ethoxycarbonyl]-phenoxy}-ethyl)-1-methyl-piperidinium |
| 32 | 4-(2-morpholin-4-yl-ethoxy)-benzoicacid cyclopropylmethoxy-4-difluoromethoxy-phenyl)-2-(3,5-dichloro-1-oxy-pyridin-4-yl)-ethyl ester |
| 33 | 4-difluoromethoxy-3-(2-piperidin-1-yl-ethoxy)-benzoic acid 2-(3,5-dichloro-1-oxy-pyridin-4-yl)-1-(3,4-dimethoxy-phenyl)-ethyl ester |
| 34 | 2-(6-methoxy-naphthalen-2-yl)-propionic acid 1-(3-cyclopropylmethoxy-4-difluoromethoxy-phenyl)-2-(3,5-dichloro-1-oxy-pyridin-4-yl)-ethyl ester |
| 35 | 4-(3,4,5-triacetoxy-6-acetoxymethyl-tetrahydro-pyran-2-yloxy)-benzoic acid 1-(3-cyclopropylmethoxy-4-difluoromethoxy-phenyl)-2-(3,5-dichloro-1-oxy-pyridin-4-yl)-ethyl ester |
| 36 | 3-cyclopropylmethoxy-4-(2-piperidin-1-yl-ethoxy)-benzoic acid 1-(3-cyclopropylmethoxy-4-difluoromethoxy-phenyl)-2-(3,5-dichloro-1-oxy-pyridin-4-yl)-ethyl ester |
| 37 | 2-(6-methoxy-naphthalen-2-yl)-propionic acid 2-(3,5-dichloro-1-oxy-pyridin-4-yl)-1-(3,4-dimethoxy-phenyl)-ethyl ester |
| 38 | 2-(6-methoxy-naphthalen-2-yl)-propionic acid 2-(3,5-dichloro-pyridin-4-yl)-1-(3,4-dimethoxy-phenyl)-ethylester |
| 39 | 2-(6-methoxy-naphthalen-2-yl)-propionic acid 1-(3-cyclopropylmethoxy-4-difluoromethoxy-phenyl)-2-(3,5-dichloro-pyridin-4-yl)-ethyl ester |
| 40 | 4-amino-benzoic acid 1-(3-cyclopropylmethoxy-4-difluoromethoxy-phenyl)-2-(3,5-dichloro-1-oxy-pyridin-4-yl)-ethyl ester |
| 41 | 2-(4-amino-phenyl)-propionic acid 1-(3-cyclopropylmethoxy-4-difluoromethoxy-phenyl)-2-(3,5-dichloro-1-oxy-pyridin-4-yl)-ethyl ester |
| 42 | 4-amino-benzoic acid 1-(3-cyclopentyloxy-4-methoxy-phenyl)-2-(3,5-dichloro-1-oxy-pyridin-4-yl)-ethyl ester |
| 43 | 4-dimethylamino-benzoic acid 1-(3-cyclopropylmethoxy-4-difluoromethoxy-phenyl)-2-(3,5-dichloro-1-oxy-pyridin-4-yl)-ethyl ester |
| 44 | terephthalic acid mono-[1-(3-cyclopropylmethoxy-4-difluoromethoxy-phenyl)-2-(3,5-dichloro-1-oxy-pyridin-4-yl)-ethyl] ester |
| 45 | 3-dimethylamino-4-methoxy-benzoic acid 1-(3-cyclopropylmethoxy-4-difluoromethoxy-phenyl)-2-(3,5-dichloro-1-oxy-pyridin-4-yl)-ethyl ester |
| 46 | 4-imidazol-1-yl-benzoic acid 1-(3-cyclopropylmethoxy-4-difluoromethoxy-phenyl)-2-(3,5-dichloro-1-oxy-pyridin-4-yl)-ethyl ester |
| 47 | 4-dimethylaminomethyl-benzoic acid 1-(3-cyclopropylmethoxy-4-difluoromethoxy-phenyl)-2-(3,5-dichloro-1-oxy-pyridin-4-yl)-ethyl ester |
| 48 | 1-methyl-1H-imidazole-4-carboxylic acid 1-(3-cyclopropylmethoxy-4-difluoromethoxy-phenyl)-2-(3,5-dichloro-1-oxy-pyridin-4-yl)-ethyl ester |

-continued

| Compound | Chemical name |
|---|---|
| 49 | 4-methanesulfonylamino-benzoic acid1-(3-cyclopropylmethoxy-4-difluoromethoxy-phenyl)-2-(3,5-dichloro-1-oxy-pyridin-4-yl)-ethyl ester |
| 50 | 3-(cyclopropylmethyl-methyl-amino)-4-methoxy-benzoic acid 1-(3-cyclopropylmethoxy-4-difluoromethoxy-phenyl)-2-(3,5-dichloro-1-oxy-pyridin-4-yl)-ethyl ester |
| 51 | 4-methyl-3,4-dihydro-2H-benzo[1,4]oxazine-7-carboxylic acid 1-(3-cyclopropylmethoxy-4-difluoromethoxy-phenyl)-2-(3,5-dichloro-1-oxy-pyridin-4-yl)-ethyl ester |
| 52 | 1,2-dimethyl-1H-benzoimidazole-5-carboxylic acid 1-(3-cyclopropylmethoxy-4-difluoromethoxy-phenyl)-2-(3,5-dichloro-1-oxy-pyridin-4-yl)-ethylester |
| 53 | quinoline-3-carboxylic acid 1-(3-cyclopropylmethoxy-4-difluoromethoxy-phenyl)-2-(3,5-dichloro-1-oxy-pyridin-4-yl)-ethyl ester |
| 54 | (1,3-dimethyl-2,6-dioxo-1,2,3,6-tetrahydro-purin-7-yl)-acetic acid 1-(3-cyclopropylmethoxy-4-difluoromethoxy-phenyl)-2-(3,5-dichloro-1-oxy-pyridin-4-yl)-ethyl ester |
| 55 | hexadecanoic acid 1-(3-cyclopropylmethoxy-4-difluoromethoxy-phenyl)-2-(3,5-dichloro-1-oxy-pyridin-4-yl)-ethyl ester |
| 56 | pentanoic acid 1-(3-cyclopropylmethoxy-4-difluoromethoxy-phenyl)-2-(3,5-dichloro-1-oxy-pyridin-4-yl)-ethyl ester |
| 58 | 3-cyclopropylmethoxy-4-difluoromethoxy-benzoic acid 1-(3-cyclopropylmethoxy-4-difluoromethoxy-phenyl)-2-(3,5-dichloro-1-oxy-pyridin-4-yl)-ethyl ester |
| 59 | 4-(3-cyclopropylmethyl-ureido)-benzoic acid 1-(3-cyclopropylmethoxy-4-difluoromethoxy-phenyl)-2-(3,5-dichloro-1-oxy-pyridin-4-yl)-ethyl ester |
| 60 | quinoline-8-carboxylic acid 1-(3-cyclopropylmethoxy-4-difluoromethoxy-phenyl)-2-(3,5-dichloro-1-oxy-pyridin-4-yl)-ethyl ester |
| 61 | 3-cyclopropylmethoxy-4-dimethylamino-benzoic acid 1-(3-cyclopropylmethoxy-4-difluoromethoxy-phenyl)-2-(3,5-dichloro-1-oxy-pyridin-4-yl)-ethyl ester |
| 62 | 4-[3-(2-methoxy-ethyl)-ureido]-benzoic acid 1-(3-cyclopropylmethoxy-4-difluoromethoxy-phenyl)-2-(3,5-dichloro-1-oxy-pyridin-4-yl)-ethyl ester |
| 63 | 1,3-dimethyl-2-oxo-2,3-dihydro-1H-benzoimidazole-5-carboxylic acid 1-(3-cyclopropylmethoxy-4-difluoromethoxy-phenyl)-2-(3,5-dichloro-1-oxy-pyridin-4-yl)-ethyl ester |
| 64 | 2-(2-fluoro-biphenyl-4-yl)-propionic acid 1-(3-cyclopropylmethoxy-4-difluoromethoxy-phenyl)-2-(3,5-dichloro-1-oxy-pyridin-4-yl)-ethyl ester |
| 65 | 3-cyclopropylmethoxy-4-difluoromethoxy-benzoic acid 1-(3-cyclopropylmethoxy-4-methoxy-phenyl)-2-(3,5-dichloro-pyridin-4-yl)-ethyl ester |
| 66 | 3-cyclopropylmethoxy-4-difluoromethoxy-benzoic acid 1-(3-cyclopropylmethoxy-4-methoxy-phenyl)-2-(3,5-dichloro-1-oxy-pyridin-4-yl)-ethyl ester |
| 67 | 2-(6-dimethylamino-naphthalen-2-yl)-propionic acid 1-(3-cyclopropylmethoxy-4-difluoromethoxy-phenyl)-2-(3,5-dichloro-1-oxy-pyridin-4-yl)-ethyl ester |
| 68 | 2-(6-dimethylamino-naphthalen-2-yl)-propionic acid 1-(3-cyclopropylmethoxy-4-difluoromethoxy-phenyl)-2-(3,5-dichloro-1-oxy-pyridin-4-yl)-ethyl ester |
| 69 | 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| 70 | 4-(3,7,12-trihydroxy-10,13-dimethyl-hexadecahydro-cyclopenta[a]phenanthren-17-yl)-pentanoic acid 1-(3-cyclopropylmethoxy-4-difluoromethoxy-phenyl)-2-(3,5-dichloro-pyridin-4-yl)-ethyl ester |
| 71 | 4-(3,7,12-trihydroxy-10,13-dimethyl-hexadecahydro-cyclopenta[a]phenanthren-17-yl)-pentanoic acid 1-(3-cyclopropylmethoxy-4-difluoromethoxy-phenyl)-2-(3,5-dichloro-1-oxy-pyridin-4-yl)-ethyl ester |
| 72 | acetic acid 1-(3-cyclopropylmethoxy-4-difluoromethoxy-phenyl)-2-(3,5-dichloro-pyridin-4-yl)-ethyl ester |
| 73 | phenyl-acetic acid 1-(3-cyclopropylmethoxy-4-difluoromethoxy-phenyl)-2-(3,5-dichloro-pyridin-4-yl)-ethyl ester |
| 74 | butyric acid 1-(3-cyclopropylmethoxy-4-difluoromethoxy-phenyl)-2-(3,5-dichloro-pyridin-4-yl)-ethyl ester |
| 75 | 4-phenyl-butyric acid 1-(3-cyclopropylmethoxydifluoromethoxy-phenyl)-2-(3,5-dichloro-pyridin-4-yl)-ethyl ester |
| 76 | 4-[3-(2-dimethylamino-ethyl)-ureido]-benzoic acid 1-(3-cyclopropylmethoxy-4-difluoromethoxy-phenyl)-2-(3,5-dichloro-1-oxy-pyridin-4-yl)-ethyl ester |

-continued

| Compound | Chemical name |
|---|---|
| 77 | 6-dimethylamino-naphthalene-2-carboxylic acid 1-(3-cyclopropylmethoxy-4-difluoromethoxy-phenyl)-2-(3,5-dichloro-1-oxy-pyridin-4-yl)-ethyl ester |
| 78 | acetoxy-phenyl-acetic acid 1-(3-cyclopropylmethoxy-4-difluoromethoxy-phenyl)-2-(3,5-dichloro-pyridin-4-yl)-ethyl ester |
| 79 | 1-(3-Methanesulfonylamino-4-methoxy-phenyl)-cyclopropanecarboxylic acid 1-(3-cyclopropylmethoxy-4-difluoromethoxy-phenyl)-2-(3,5-dichloro-1-oxy-pyridin-4-yl)-ethyl ester |
| 80 | 1-[3-(Cyclopropylmethyl-methyl-amino)-4-methoxy-phenyl]-cyclopropanecarboxylic acid 1-(3-cyclopropylmethoxy-4-difluoromethoxy-phenyl)-2-(3,5-dichloro-1-oxy-pyridin-4-yl)-ethylester |
| 81 | oxy-benzoic acid 1-(3-cyclopentyloxy-4-methoxy-phenyl)-2-(3,5-dichloro-pyridin-4-yl)-ethyl ester |
| 82 | 2,3-dihydro-benzo[1,4]dioxine-6-carboxylic acid 1-(3-cyclopropylmethoxy-4-difluoromethoxy-phenyl)-2-(3,5-dichloro-pyridin-4-yl)-ethyl ester |
| 83 | 3-cyclopropylmethoxy-4-difluoromethoxy-benzoic acid 2-(3,5-dichloro-pyridin-4-yl)-1-(2,2-difluoro-benzo[1,3]dioxol-5-yl)-ethyl ester |
| 84 | 3-cyclopropylmethoxy-4-difluoromethoxy-benzoic acid 2-(3,5-dichloro-pyridin-4-yl)-1-(2,3-dihydro-benzo[1,4]dioxin-6-yl)-ethyl ester |
| 85 | 3,4,5-triethoxy-benzoic acid 1-(3-cyclopropylmethoxy-4-difluoromethoxy-phenyl)-2-(3,5-dichloro-pyridin-4-yl)-ethyl ester |
| 86 | 4-fluoro-3-methoxy-benzoic acid 1-(3-cyclopropylmethoxy-4-difluoromethoxy-phenyl)-2-(3,5-dichloro-pyridin-4-yl)-ethyl ester |
| 87 | 1-methoxy-naphthalene-2-carboxylic acid 1-(3-cyclopropylmethoxy-4-difluoromethoxy-phenyl)-2-(3,5-dichloro-pyridin-4-yl)-ethyl ester |
| 88 | 3,4,5-trifluoro-benzoic acid 1-(3-cyclopropylmethoxy-4-difluoromethoxy-phenyl)-2-(3,5-dichloro-pyridin-4-yl)-ethyl ester |
| 89 | 2-(2-fluoro-biphenyl-4-yl)-propionic acid 1-(3-cyclopropylmethoxy-4-difluoromethoxy-phenyl)-2-(3,5-dichloro-1-oxy-pyridin-4-yl)-ethyl ester |
| 90 | 2-oxo-thiazolidine-4-carboxylic acid 1-(3-cyclopropylmethoxy-4-difluoromethoxy-phenyl)-2-(3,5-dichloro-1-oxy-pyridin-4-yl)-ethyl ester |
| 91 | 4-methyl-3,4-dihydro-2H-benzo[1,4]oxazine-7-carboxylic acid 1-(3-cyclopropylmethoxy-4-difluoromethoxy-phenyl)-2-(3,5-dichloro-pyridin-4-yl)-ethyl ester |
| 92 | 1-cyclopropylmethyl-3-methyl-2-oxo-2,3-dihydro-1H-benzoimidazole-5-carboxylic acid 1-(3-cyclopropylmethoxy-4-difluoromethoxy-phenyl)-2-(3,5-dichloro-1-oxy-pyridin-4-yl)ethyl ester |
| 93 | 1-(3',4'-dichloro-2-fluoro-biphenyl-4-yl)-cyclopropanecarboxylic acid 1-(3-cyclopropylmethoxy-4-difluoromethoxy-phenyl)-2-(3,5-dichloro-1-oxy-pyridin-4-yl)-ethyl ester |
| 94 | 2,3-dihydro-benzo[1,4]dioxine-6-carboxylic acid 1-(3-cyclopropylmethoxy-4-difluoromethoxy-phenyl)-2-(3,5-dichloro-1-oxy-pyridin-4-yl)-ethyl ester |
| 95 | 6-dimethylamino-naphthalene-2-carboxylic acid 1-(3-cyclopropylmethoxy-4-difluoromethoxy-phenyl)-2-(3,5-dichloro-pyridin-4-yl)-ethyl ester |
| 96 | 1-cyclopropylmethyl-1H-indole-5-carboxylic acid 1-(3-cyclopropylmethoxy-4-difluoromethoxy-phenyl)-2-(3,5-dichloro-1-oxy-pyridin-4-yl)-ethyl ester |
| 97 | 4,7,7-trimethyl-3-oxo-2-oxa-bicyclo[2.2.1]heptane-1-carboxylic acid 1-(3-cyclopropylmethoxy-4-difluoromethoxy-phenyl)-2-(3,5-dichloro-1-oxy-pyridin-4-yl)-ethyl ester |
| 98 | 2-benzyloxy-propionic acid 1-(3-cyclopropylmethoxy-4-difluoromethoxy-phenyl)-2-(3,5-dichloro-1-oxy-pyridin-4-yl)-ethyl ester |
| 99 | (3,4-dimethoxy-phenylsulfanyl)-acetic acid 1-(3-cyclopropylmethoxy-4-difluoromethoxy-phenyl)-2-(3,5-dichloro-1-oxy-pyridin-4-yl)-ethyl ester |
| 100 | 4-methanesulfonylamino-benzoic acid1-(3-cyclopropylmethoxy-4-difluoromethoxy-phenyl)-2-(3,5-dichloro-pyridin-4-yl)-ethyl ester |
| 101 | 4-[9-(4-ethyl-phenoxy)-nonyloxy]-benzoic acid 1-(3-cyclopropylmethoxy-4-difluoromethoxy-phenyl)-2-(3,5-dichloro-pyridin-4-yl)-ethyl ester |

Advantageously the compounds of the invention are characterized by selectivity toward LPDE4 higher than that toward HPDE4 as obtained by the determination of their $IC_{50}$. In the case of LPDE4, the $IC_{50}$ is the molar concentration of the test compound producing 50% inhibition of cAMP disappearance, assessed as described in Cortijo, J. et al., *Br. J. Pharmacol.*, 1993, 108: 562-568, while in the case of HPDE4, the $IC_{50}$ is the molar concentration of the test compound producing 50% inhibition of the binding of [$H^3$] rolipram, assessed as described in Duplantier, A. J. et al., *J. Med. Chem.*, 1996; 39: 120-125. Preferably the HPDE4/LPDE4 $IC_{50}$ ratio for the compounds of the invention is higher than 5, preferably higher than 10, more preferably higher than 20 and even more preferably higher than 100.

The compounds of general formula (I) may be prepared conventionally according to methods disclosed in the art. Some of the processes which can be used are described below and reported in Scheme 1 and should not be viewed as limiting the scope of the synthetic methods available for the preparation of the compounds of the invention.

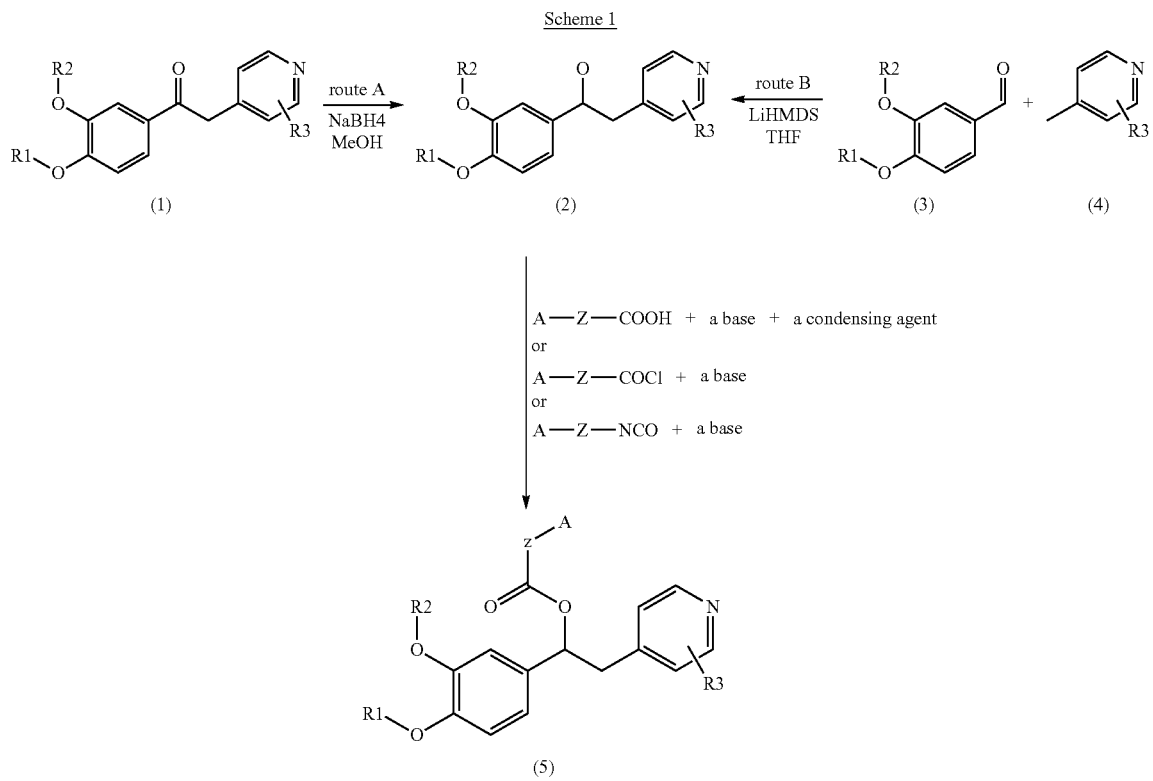

Scheme 1

For instance, according to a particular embodiment of the present invention (scheme 1), the compounds of general formula (5) may be prepared according to a process which includes the following steps:

$1^{st}$ step—Reducing an ethanone derivative of general formula (1) to give an alcohol derivative of general formula (2) (route A). The reaction may be carried out by using sodium boron hydride ($NaBH_4$) in a solvent such as methanol at room temperature under nitrogen atmosphere.

$2^{nd}$ step—Adding a suitable acid of formula AZCOOH to a solution of the alcohol derivative of general formula (2) to give a compound of general formula (5). The reaction is carried out in the presence of a suitable strong base such as lithium diisopropylamide (LDA), NaH, dimethylaminopyridine (DMAP) and in the presence of a condensing agent such as 1-Ethyl-3-[3-dimethylaminopropyl]carbodiimide hydrochloride (EDC) and N-hydroxybenzotriazole (HOBT) in a solvent such as dichloromethane under nitrogen atmosphere. Other solvents may be used, such as dimethylformamide (DMF), tetrahydrofuran (THF), chloroform, dioxane and any other aprotic solvent known to those skilled in the art. In a particular embodiment, the reaction may also be carried out in absence of solvents.

In case the carboxylic acid A-Z—COOH bears reactive groups like hydroxyl, carboxyl, thio or amino groups, they may need to be protected by protecting groups such as t-buthoxycarbonyl, benzyl, benzyloxycarbonyl, methyl, trimethylsilyl and similar and, at a certain step of the synthesis, deprotected to obtain again the free reactive group; the deprotected group may be then reacted with suitable reagents like alkylating, acylating, sulphonylating agents or similar.

The protection and deprotection of functional groups is described in Protective *Groups in Organic Chemistry*, 3rd edition, T. W. Greene and P. G. M. Wuts, Wiley-Interscience (1999) and *Protecting Groups*, P. J. Kocienski, Georg Thieme Verlag (1994).

Compounds of general formula (5) may be also prepared by adding a suitable acyl chloride of general formula A-Z—COCl or a suitable isocyanate of general formula A-Z—NCO to a solution of the alcohol derivative of general formula (2), with a suitable base in a stoichiometric or a catalytic amount, according to procedures well known to the skilled person.

The alcohol derivative of general formula (2) may alternatively be prepared by reacting a benzaldehyde derivative of formula (3) with a methylpyridine derivative of formula (4) (route B) using lithium-bis-(trimethylsilyl)-amide (LiHMDS) or similar strong bases and a solvent such as tetrahydrofuran (THF) or other aprotic solvents. Intermediates of general formula (3) and (4) are commercially available or may be prepared according to methods available in the literature and well known to the person skilled in the art.

The N-oxides on the 2-pyridinyl ring of the compounds of general formula (5) may be prepared according to methods available in the literature and well known to the skilled person. For instance they may be prepared by dissolving the compound of general formula (5) in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

For those compounds in which A is a ring substituted with a functional group sensitive to oxidation, the corresponding N-oxides are alternatively prepared by carrying out the oxidation step before the $2^{nd}$ step of the route A.

The present invention also provides pharmaceutical compositions of compounds of general formula (I) in admixture with one or more pharmaceutically acceptable carriers, for example those described in *Remington's Pharmaceutical Sciences Handbook*, XVII Ed., Mack Pub., N.Y., U.S.A.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering the compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols. Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable preparations include inhalable powders, propellant-containing metering aerosols or propellant-free inhalable formulations.

For administration as a dry powder, single- or multi-dose inhalers known from the prior art may be utilized. In that case, the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta$_2$-agonists, corticosteroids and anticholinergic or antimuscarinic agents.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of general formula (I) may be administered for example, at a dosage comprised between 0.001 and 1000 mg/day, preferably between 0.1 and 500 mg/day.

When they are administered by inhalation route, the dosage of the compounds of general formula (I) is advantageously comprised between 0.01 and 20 mg/day, preferably between 0.1 and 10 mg/day.

Preferably, the compounds of general formula (I) alone or combined with other active ingredients may be administered for the prevention and/or treatment of any obstructive respiratory disease such as asthma, chronic bronchitis and chronic obstructive pulmonary disease (COPD).

However the compounds of general formula (I) may be administered for the prevention and/or treatment of any disease wherein PDE4 inhibition is required. Such diseases include: allergic disease states such as atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritis in the anogenital area, alopecia greata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Example 1

Preparation of 3,5-dichloro-4-methylpyridine (Intermediate (4) of Scheme 1)

Diisopropylamine (70 mL, 500 mmol) was dissolved in dry tetrahydrofuran (THF) (500 mL), the solution was cooled to −10° C. and buthyl lithium (2.5 N in hexane, 210 mL, 525 mmol) was added dropwise under stirring. After 30 minutes the solution was cooled to −20° C. and 3,5-dicholopyridine (66.6 g, 450 mmol) in tetrahydrofuran (200 mL) was added dropwise. The solution was stirred at −10° C. for 30 minutes, cooled to −70° C. and added dropwise with iodomethane (50 mL, 1.6 mol) in tetrahydrofuran (100 mL). The reaction mixture was allowed to warm to room temperature, quenched with water (100 mL) and extracted with diethyl ether (3×100 mL); the combined organic layers were dried over sodium sulphate (5 g) and evaporated to dryness. The crude product was crystallized twice from aqueous ethanol than from hexane to afford 3,5-dichloro-4-methylpyridine (49.9 g, 306 mmol, 68% yield) as a white solid.

MS/ESI$^+$ 162-164-166 m/z [MH]$^+$.

Example 2

Preparation of 2-(3,5-dichloro-pyridin-4-yl)-1-(3,4-dimethoxy-phenyl)-ethanone (Intermediate (1) of Scheme 1)

A solution of 3,5-dichloro-4-methyl-pyridine (2.06 g, 12.7 mmol) in dry tetrahydrofuran (30 ml) was cooled down to −78° C., then a 1.8 M solution of lithium diisopropylamide in tetrahydrofuran (7.4 ml, 13.3 mmol) was added dropwise under stirring, keeping the temperature below −70° C. The resulting solution was stirred for 30 min., then a solution of 3,4-dimethoxy-benzoyl chloride (2.55 g, 12.7 mmol) in dry tetrahydrofuran (20 ml) was added dropwise, maintaining the temperature below −70° C. After stirring for 15 minutes, ice (20 g) was added, followed by further 500 ml of water. The mixture was extracted with ethyl acetate (2×50 ml), the combined organic layers were dried over sodium sulphate and evaporated under reduced pressure to give an oil that was purified by flash chromatography (Eluent: ethyl acetate/petroleum ether from 10/90 to 30/70 v:v). 2.1 grams (6.4 mmol, 52% yield) of the title compound were obtained as a white solid.

MS/ESI$^+$ 326-328-330 m/z [MH]$^+$; $^1$H NMR (CDCl$_3$ calibrated at 7.26 ppm) δ 3.91 and 3.95 (2s, 6H), 4.62 (s, 2H), 6.91-6.95 (d, 1H), 7.53-7.54 (d, 1H), 7.67-7.75 (dd, 1H), 8.49 (s, 2H).

The following intermediates were prepared using said route with suitable solvents:

TABLE 1

| Intermediate | R$_1$ | R$_2$ | R$_3$ | Analytical |
|---|---|---|---|---|
| 1 | Me | cyclopentyl | 3,5 dichloro | MS/ESI$^+$ 326-328-330 [MH]$^+$ |
| 1a | Me | cyclopropylmethyl | 3,5 dichloro | MS/ESI$^+$ 366-368-370 [MH]$^+$ |
| 1b | difluoromethyl | cyclopropylmethyl | 3,5 dichloro | MS/ESI$^+$ 402-404-406 [MH]$^+$ |
| 1c | difluoromethyl | difluoromethyl | 3,5 dichloro | MS/ESI$^+$ 398-400-402 [MH]$^+$ |
| 1d | difluoromethyl | Me | 3,5 dichloro | MS/ESI$^+$ 362-366-368 [MH]$^+$ |
| 1e | difluoromethyl | cyclopentyl | 3,5 dichloro | MS/ESI$^+$ 416-418-420 [MH]$^+$ |

Example 3

Preparation of 2-(3,5-dichloro-pyridin-4-yl)-1-(3,4-dimethoxy-phenyl)-ethanol (Intermediate (2) of Scheme 1)

Route A.

Sodium boron hydride NaBH$_4$ (45.2 mg, 2.5 eq.) is added to a suspension of 2-(3,5-dichloro-pyridin-4-yl)-1-(3,4-dimethoxy-phenyl)-ethanone (150 mg, 1 eq.) in CH$_3$OH (5 ml), at room temperature under nitrogen atmosphere. The mixture is stirred at room temperature overnight, then the reaction is quenched with water and extracted with EtOAc. The organic layer is dried over Na$_2$SO$_4$ and the solvent is evaporated. The crude is purified by flash chromatography on silica gel in gradient elution from petroleum ether/EtOAc 9/1 v/v to petroleum ether/EtOAc 7/3 v/v, to obtain 75 mg of the title compound (50% yield).

MS/ESI$^+$ 328-330-332 [MH]$^+$

The following intermediates were prepared using said route with suitable solvents:

TABLE 2

| Intermediates | R$_1$ | R$_2$ | R$_3$ | Analytical |
|---|---|---|---|---|
| 2 | Me | cyclopentyl | 3,5-dichloro | MS/ESI$^+$ 328-330-332 [MH]$^+$ |
| 2a | Me | cyclopropylmethyl | 3,5-dichloro | MS/ESI$^+$ 368-370-372 [MH]$^+$ |
| 2b | difluoromethyl | cyclopropylmethyl | 3,5-dichloro | MS/ESI$^+$ 404-406-408 [MH]$^+$ |
| 2c | difluoromethyl | difluoromethyl | 3,5-dichloro | MS/ESI$^+$ 400-402-404 [MH]$^+$ |
| 2d | difluoromethyl | Me | 3,5-dichloro | MS/ESI$^+$ 364-368-370 [MH]$^+$ |

Example 4

Preparation of 2-(3,5-dichloro-pyridin-4-yl)-1-(3,4-dimethoxy-phenyl)-ethanol (Intermediate (2) of Scheme 1)

Route B.

3,5-Dichloro-4-methylpyridine (500 mg, 1 eq.) is dissolved in dry THF (2 mL) under nitrogen atmosphere at −60° C. LiN(TMS)$_2$ (1.0M in THF, 3.38 mL, 1.1 eq.) is added dropwise via syringe, keeping the temperature below −55° C. The mixture turns yellow and is stirred at −60° C. for about 30 minutes. Then a solution of 3,4-dimethoxybenzaldehyde (513 mg, 1 eq.) in dry THF (2 mL) is added dropwise via syringe, keeping the temperature below −55° C. After the addition the mixture is slowly warmed to room temperature and stirred at room temperature for about 2 hours. Then it is quenched with water and extracted with EtOAc. The organic layer is dried over Na$_2$SO$_4$ and the solvent is evaporated. The crude is triturated with Et$_2$O, and filtered to obtain 741 mg of the title compound as a white solid (73% yield). MS/ESI$^+$ 328-330-332 [MH]$^+$

Example 5

Preparation of (S)-2-(4-isobutyl-phenyl)-propionic acid 2-(3,5-dichloro-pyridin-4-yl)-1-(3,4-dimethoxy-phenyl)-ethyl ester (Compound 1)

(1-Ethyl-3-[3-dimethylaminopropyl]carbodiimide hydrochloride) (EDC.HCl) (345 mg, 3 eq.) is added to a solution of 2-(3,5-dichloro-pyridin-4-yl)-1-(3,4-dimethoxy-phenyl)-ethanol (200 mg, 1 eq.), (S)-2-(4-isobutyl-phenyl)-propionic acid (148 mg, 1.2 eq.) and 4-dimethylaminopyridine (DMAP) (37 mg, 0.5 eq.) in dry CH$_2$Cl$_2$ (8 mL) at room temperature under nitrogen atmosphere. The mixture is stirred at room temperature overnight, then it is treated with a saturated solution of NH$_4$Cl (20 ml) and extracted with EtOAc (2×20 ml). The combined organic layer are dried over Na$_2$SO$_4$ and the solvent is evaporated. The crude is purified by flash chromatography on silica gel in gradient elution (from petroleum ether/EtOAc 9/1 v/v to petroleum ether/EtOAc 7/3 v/v) to yield 259 mg of pure compound.

The following compounds were prepared using said route with suitable reagents:

TABLE 3

| Compound | R$_1$ | R$_2$ | Z—A | Analytical |
|---|---|---|---|---|
| 1 | Me | Me | (S)-1-(4-isobutylphenyl)ethyl | MS/ESI$^+$ 516-518-520 [MH]$^+$; $^1$H NMR (CDCl$_3$ calibrated at 7.26 ppm, mix of diast.) δ: 8.47 and 8.31 (s*, 1H); 7.05 (m*, 4H); 6.96-6.63 (m*, 3H); 6.10 (m*, 1H); 3.89 and 3.86 (s*, 3H); 3.86 and 3.70 (s*, 3H); 3.69-3.49 (m*, 2H); 3.24 (m*, 1H); 2.48 and 2.46 (d*, 2H); 1.88 (m*, 1H); 1.39 (d*, 3H); 0.94 and 0.92 (d*, 3H). |
| 2 | Me | Me | benzyl | MS/ESI$^+$ 446-448-450 [MH]$^+$; $^1$H NMR (CDCl$_3$ calibrated at 7.26 ppm) δ: 8.42 (s*, 2H); 7.26 (m*, 3H); 7.17 (m*, 2H); 6.89 (dd*, 1H); 6.82 (d*, 1H); 6.79 (d*, 1H); 6.14 (dd*, 1H); 3.89 (s*, 3H); 3.80 (s*, 3H); 3.61 (dd*, 1H); 3.58 and 3.55 (ABq, 2H); 3.29 (dd*, 1H). |
| 3 | Me | Me | 1-phenylcyclopropyl | MS/ESI$^+$ 472-474-476 [MH]$^+$; $^1$H NMR (CDCl$_3$ calibrated at 7.26 ppm) δ: 8.45 (s*, 2H); 7.34-7.26 (m*, 5H); 6.79 (m*, 2H); 6.68 (m*, 1H); 6.15 (dd*, 1H); 3.89 (s*, 3H); 3.80 (s*, 3H); 3.49 (dd*, 1H); 3.15 (dd*, 1H); 1.54 (m*, 1H); 1.43 (m*, 1H); 1.22 (m*, 1H); 1.10 (m*, 1H). |

TABLE 3-continued

| Compound | R₁ | R₂ | Z—A | Analytical |
|---|---|---|---|---|
| 4 | Me | Me | 3,4-dimethoxyphenyl | MS/ESI⁺ 492-494-496 [MH]⁺; ¹H NMR (CDCl₃ calibrated at 7.26 ppm) δ: 8.47 (s*, 1H); 7.72 (dd*, 1H); 7.54 (d*, 1H); 7.04 (dd*, 1H); 7.01 (d*, 1H); 6.89 (d*, 1H); 6.88 (d*, 1H); 6.34 (dd*, 1H); 3.95 (s*, 3H); 3.93 (s*, 3H); 3.91 (s*, 3H); 3.89 (s*, 3H); 3.82 (dd*, 1H); 3.41 (dd*, 1H). |
| 5 | CHF₂ | cyclopropyl-methyl | (R)-NHBoc-α-methylbenzyl | MS/ESI⁺ 637-639-641 [MH]⁺; ¹H NMR (CDCl₃ calibrated at 7.26 ppm) δ: 8.21 (s*, 2H), 7.36-7.22 (m*, 3H), 7.16 (m*, 3H), 7.00 (m*, 2H), 6.65 (dd*, 1H), 6.09 (dd*, 1H), 5.31 (br* s*, 2H), 3.93 (d*, 2H), 3.54 (dd*, 1H), 3.17 (dd*, 1H), 1.40 (s*, 9H), 1.30 (m*, 1H); 0.68 (m*, 2H), 0.42 (m*, 2H). |
| 6 | CHF₂ | cyclopropyl-methyl | (S)-NHBoc-α-methylbenzyl | MS/ESI⁺ 637-639-641 [MH]⁺; ¹H NMR (CDCl₃ calibrated at 7.26 ppm) δ: 8.21 (s*, 2H), 7.36-7.22 (m*, 3H), 7.16 (m*, 3H), 7.00 (m*, 2H), 6.65 (dd*, 1H), 6.09 (dd*, 1H), 5.31 (br* s*, 2H), 3.93 (d*, 2H), 3.54 (dd*, 1H), 3.17 (dd*, 1H), 1.40 (s*, 9H), 1.30 (m*, 1H); 0.68 (m*, 2H), 0.42 (m*, 2H). |
| 7 | CHF₂ | cyclopropyl-methyl | NH₂-α-methylbenzyl | MS/ESI⁺ 537-539-541 [MH]⁺; ¹H NMR (CDCl₃ calibrated at 7.26 ppm, mix of diast.) δ: 8.49 and 8.19 (s* 2H); 7.40-7.22 (m*, 3H); 7.17 (m*, 2H); 6.97 (m*, 2H); 6.63 and 6.57 (dd*, 1H); 6.53 (m*, 1H); 6.08 and 6.04 (dd*, 1H); 3.90 (d*, 2H); 3.64-3.44 (m*, 2H); 3.24 and 3.13 (dd*, 1H); 1.22 (m*, 1H); 0.66 (m*, 2H); 0.36 (m*, 2H). |

TABLE 3-continued

| Compound | R₁ | R₂ | Z—A | Analytical |
|---|---|---|---|---|
| 8 | CHF₂ | cyclopropyl-methyl | (S)-1-phenylethylamine attached via *CH(NH₂)-phenyl | MS/ESI⁺ 537-539-541 [MH]⁺; ¹H NMR (CDCl₃ calibrated at 7.26 ppm) δ: 8.25 (s*, 2 H), 7.35-7.22 (m*, 3 H), 7.18 (m*, 3 H), 6.99 (dd*, 1 H), 6.94 (d*, 1 H), 6.64 (dd*, 1 H), 6.10 (dd*, 1 H), 4.52 (s*, 1 H), 3.87 (m*, 2 H), 3.55 (dd*, 1 H), 3.13 (dd*, 1 H), 1.74 (br* s*, 2 H), 1.30 (m*, 1 H), 0.69 (m*, 2 H), 0.40 (m*, 2 H) |
| 9 | Me | cyclopentyl | *CH(CH₃)-(4-isobutylphenyl) | MS/ESI⁺ 570-572-574 [MH]⁺; ¹H NMR (CDCl₃ calibrated at 7.26 ppm) δ: 8.46 (s*, 2H), 7.04 (m*, 4H), 6.72 (d*, 1H), 6.71 (d*, 1H), 6.67 (dd*, 1H), 6.06 (dd*, 1H), 4.60 (m*, 1H), 3.82 (s*, 3H), 3.65 (q*, 1H), 3.56 (dd*, 1H), 3.26 (dd*, 1H), 2.45 (d*, 2H), 1.95-1.75 (m*, 7H), 1.70-1.54 (m*, 2H), 1.39 (d*, 3H), 0.91 (d*, 6H) and 8.30 (s*, 2H), 7.04 (m*, 4H), 6.89 (dd*, 1H), 6.88 (d*, 1H), 6.82 (d*, 1H), 6.10 (dd*, 1H), 4.75 (m*, 1H), 3.85 (s*, 3H), 3.63 (q*, 1H), 3.56 (dd*, 1H), 3.19 (dd*, 1H), 2.47 (d*, 2H), 1.95-1.75 (m*, 7H), 1.70-1.54 (m*, 2H), 1.38 (d*, 3H), 0.93 (d*, 6H). |
| 10 | Me | Me | *CH(CH₃)-(4-nitrophenyl) | MS/ESI⁺ 505-507-509 [MH]⁺ |
| 11 | CHF₂ | Cyclopropyl-methyl | 4-substituted phenyl with 3-O-CH₂-cyclopropyl and 2-O-CHF₂ | MS/ESI⁺ 644-646-648 [MH]⁺; 1H NMR (CDCl3 calibrated at 7.26 ppm): 8.48 (s*, 2H); 7.66 (dd*, 1H); 7.58 (d*, 1H); 7.21 (d*, 1H); 7.19 (d*, 1H); 7.08 (dd*, 1H); 7.04 (dd*, 1H); 6.72 (dd*, 1H); 6.63 (dd*, 1H); 6.30 (dd*, 1H); 3.92 (d*, 2H); 3.90 (d*, 2H); 3.73 (dd*, 1H); 3.39 (dd*, 1H); 1.29 (m*, 2H); 0.68 (m*, 4H); 0.38 (m*, 4H). |

TABLE 3-continued

| Compound | R₁ | R₂ | Z—A | Analytical |
|---|---|---|---|---|
| 12 | CHF₂ | cyclopropyl-methyl | *-(CH(CH₃))-C₆H₄-CH₂CH(CH₃)₂ | MS/ESI⁺ 593-595-597 [MH]⁺ |

Example 6

Preparation of (S)-2-(4-isobutyl-phenyl)-propionic acid 2-(3,5-dichloro-1-oxy-pyridin-4-yl)-1-(3,4-dimethoxy-phenyl)-ethyl ester (Compound 13)

Compound 1 (51.5 mg, 0.1 mmoles) is dissolved in CH₂CL₂ (1 mL). m-Chloro perbenzoic acid (mCPBA, 15 mg, 0.12 mmoles) is added and the resulting solution is stirred at room temperature for 2 hours. The mixture is then diluted with CH₂Cl₂ (5 mL) and extracted with 1N NaOH (5 ml). The organic phase is dried over Na₂SO₄ and the solvent is evaporated. The crude is purified by preparative HPLC to yield 37 mg of the title compound.

The following compounds were prepared following the same route using suitable reagents:

TABLE 4

| Compound | R₁ | R₂ | Z—A | Analytical |
|---|---|---|---|---|
| 13 | Me | Me | *-(CH(CH₃))-C₆H₄-CH₂CH(CH₃)₂ | MS/ESI⁺ 532-534-536 [MH]⁺; ¹H NMR (CDCl₃ calibrated at 7.26 ppm, mix of diast), δ: 8.11 and 7.89 (s*, 2 H), 6.97-7.10 (m*, 4 H), 6.79-6.94 and 6.53-6.76 (m*, 3 H), 5.96 and 6.05 (dd*, 1 H), 3.82 and 3.82 (s*, 3 H), 3.67 and 3.82 (s*, 3 H), 3.60 (m*, 1 H), 3.41 and 3.46 (dd*, 1 H), 3.08 and 3.17 (dd*, 1 H), 2.43 and 2.49 (d*, 2 H), 1.74-1.93 (m*, 1 H), 1.36 and 1.39 (d*, 3 H), 0.88 and 0.90 (d*, 6 H) |
| 14 | CHF₂ | cyclopropyl-methyl | *-C₆H₃(OCH₂-cyclopropyl)(OCHF₂) | MS/ESI+ 660-662-664 [MH]⁺; 1H NMR (CDCl3 calibrated at 7.26 ppm): 8.25 (s*, 2 H), 7.65 (dd*, 1 H), 7.57 (d*, 1 H), 7.22 (d*, 1 H), 7.21 (d*, 1 H), 7.01-7.10 (m*, 2 H), 6.73 (t*, 1 H), 6.63 (t*, 1 H), 6.29 (dd*, 1 H), 3.92 (d*, 2 H), 3.91 (d*, 2 H), 3.73 (dd*, 1 H), 3.36 (dd*, 1 H), 1.18-1.43 (m*, 2 H), 0.56-0.77 (m*, 4 H), 0.23-0.50 (m*, 4 H) |

TABLE 4-continued

| Compound | R₁ | R₂ | Z—A | Analytical |
|---|---|---|---|---|
| 15 | CHF$_2$ | cyclopropyl-methyl | (S)-1-(4-isobutylphenyl)ethyl | MS/ESI⁺ 609-611-613 [MH]⁺ |

The following compounds were prepared in an analogous manner to the methods already described in earlier Examples, with appropriate selection of reagents and according to the general synthesis earlier described:

| Compound | Chemical name |
|---|---|
| 26 | 3-cyclopropylmethoxy-4-difluoromethoxy-benzoic acid 1-(3-cyclopentyloxy-4-methoxy-phenyl)-2-(3,5-dichloro-1-oxy-pyridin-4-yl)-ethyl ester |
| 27 | 4-(2-piperidin-1-yl-ethoxy)-benzoicacid 2-(3,5-dichloro-1-oxy-pyridin-4-yl)-1-(3,4-dimethoxy-phenyl)-ethyl ester |
| 28 | isonicotinic acid 1-(3-cyclopropylmethoxy-4-difluoromethoxy-phenyl)-2-(3,5-dichloro-1-oxy-pyridin-4-yl)-ethyl ester |
| 29 | nicotinic acid 1-(3-cyclopropylmethoxy-4-difluoromethoxy-phenyl)-2-(3,5-dichloro-1-oxy-pyridin-4-yl)-ethyl ester |
| 30 | 4-(2-imidazol-1-yl-ethoxy)-benzoic acid 1-cyclopropylmethoxy-4-difluoromethoxy-phenyl)-2-(3,5-dichloro-1-oxy-pyridin-4-yl)-ethyl ester |
| 31 | 1-(2-{4-[1-(3-cyclopropylmethoxy-4-difluoromethoxy-phenyl)-2-(3,5-dichloro-1-oxy-pyridin-4-yl)-ethoxycarbonyl]-phenoxy}-ethyl)-1-methyl-piperidinium |
| 32 | 4-(2-morpholin-4-yl-ethoxy)-benzoicacid cyclopropylmethoxy-4-difluoromethoxy-phenyl)-2-(3,5-dichloro-1-oxy-pyridin-4-yl)-ethyl ester |
| 33 | 4-difluoromethoxy-3-(2-piperidin-1-yl-ethoxy)-benzoic acid 2-(3,5-dichloro-1-oxy-pyridin-4-yl)-1-(3,4-dimethoxy-phenyl)-ethyl ester |
| 34 | 2-(6-methoxy-naphthalen-2-yl)-propionic acid 1-(3-cyclopropylmethoxy-4-difluoromethoxy-phenyl)-2-(3,5-dichloro-1-oxy-pyridin-4-yl)-ethyl ester |
| 35 | 4-(3,4,5-triacetoxy-6-acetoxymethyl-tetrahydro-pyran-2-yloxy)-benzoic acid 1-(3-cyclopropylmethoxy-4-difluoromethoxy-phenyl)-2-(3,5-dichloro-1-oxy-pyridin-4-yl)-ethyl ester |
| 36 | 3-cyclopropylmethoxy-4-(2-piperidin-1-yl-ethoxy)-benzoic acid 1-(3-cyclopropylmethoxy-4-difluoromethoxy-phenyl)-2-(3,5-dichloro-1-oxy-pyridin-4-yl)-ethyl ester |
| 37 | 2-(6-methoxy-naphthalen-2-yl)-propionic acid 2-(3,5-dichloro-1-oxy-pyridin-4-yl)-1-(3,4-dimethoxy-phenyl)-ethyl ester |
| 38 | 2-(6-methoxy-naphthalen-2-yl)-propionic acid 2-(3,5-dichloro-pyridin-4-yl)-1-(3,4-dimethoxy-phenyl)-ethylester |
| 39 | 2-(6-methoxy-naphthalen-2-yl)-propionic acid 1-(3-cyclopropylmethoxy-4-difluoromethoxy-phenyl)-2-(3,5-dichloro-pyridin-4-yl)-ethyl ester |
| 40 | 4-amino-benzoic acid 1-(3-cyclopropylmethoxy-4-difluoromethoxy-phenyl)-2-(3,5-dichloro-1-oxy-pyridin-4-yl)-ethyl ester |
| 41 | 2-(4-amino-phenyl)-propionic acid 1-(3-cyclopropylmethoxy-4-difluoromethoxy-phenyl)-2-(3,5-dichloro-1-oxy-pyridin-4-yl)-ethyl ester |
| 42 | 4-amino-benzoic acid 1-(3-cyclopentyloxy-4-methoxy-phenyl)-2-(3,5-dichloro-1-oxy-pyridin-4-yl)-ethyl ester |
| 43 | 4-dimethylamino-benzoic acid 1-(3-cyclopropylmethoxy-4-difluoromethoxy-phenyl)-2-(3,5-dichloro-1-oxy-pyridin-4-yl)-ethyl ester |
| 44 | terephthalic acid mono-[1-(3-cyclopropylmethoxy-4-difluoromethoxy-phenyl)-2-(3,5-dichloro-1-oxy-pyridin-4-yl)-ethyl] ester |

| Compound | Chemical name |
|---|---|
| 45 | 3-dimethylamino-4-methoxy-benzoic acid 1-(3-cyclopropylmethoxy-4-difluoromethoxy-phenyl)-2-(3,5-dichloro-1-oxy-pyridin-4-yl)-ethyl ester |
| 46 | 4-imidazol-1-yl-benzoic acid 1-(3-cyclopropylmethoxy-4-difluoromethoxy-phenyl)-2-(3,5-dichloro-1-oxy-pyridin-4-yl)-ethyl ester |
| 47 | 4-dimethylaminomethyl-benzoic acid 1-(3-cyclopropylmethoxy-4-difluoromethoxy-phenyl)-2-(3,5-dichloro-1-oxy-pyridin-4-yl)-ethyl ester |
| 48 | 1-methyl-1H-imidazole-4-carboxylic acid 1-(3-cyclopropylmethoxy-4-difluoromethoxy-phenyl)-2-(3,5-dichloro-1-oxy-pyridin-4-yl)-ethyl ester |
| 49 | 4-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| 50 | 3-(cyclopropylmethyl-methyl-amino)-4-methoxy-benzoic acid 1-(3-cyclopropylmethoxy-4-difluoromethoxy-phenyl)-2-(3,5-dichloro-1-oxy-pyridin-4-yl)-ethyl ester |
| 51 | 4-methyl-3,4-dihydro-2H-benzo[1,4]oxazine-7-carboxylic acid 1-(3-cyclopropylmethoxy-4-difluoromethoxy-phenyl)-2-(3,5-dichloro-1-oxy-pyridin-4-yl)-ethyl ester |
| 52 | 1,2-dimethyl-1H-benzoimidazole-5-carboxylic acid 1-(3-cyclopropylmethoxy-4-difluoromethoxy-phenyl)-2-(3,5-dichloro-1-oxy-pyridin-4-yl)-ethylester |
| 53 | quinoline-3-carboxylic acid 1-(3-cyclopropylmethoxy-4-difluoromethoxy-phenyl)-2-(3,5-dichloro-1-oxy-pyridin-4-yl)-ethyl ester |
| 54 | (1,3-dimethyl-2,6-dioxo-1,2,3,6-tetrahydro-purin-7-yl)-acetic acid 1-(3-cyclopropylmethoxy-4-difluoromethoxy-phenyl)-2-(3,5-dichloro-1-oxy-pyridin-4-yl)-ethyl ester |
| 55 | hexadecanoic acid 1-(3-cyclopropylmethoxy-4-difluoromethoxy-phenyl)-2-(3,5-dichloro-1-oxy-pyridin-4-yl)-ethyl ester |
| 56 | pentanoic acid 1-(3-cyclopropylmethoxy-4-difluoromethoxy-phenyl)-2-(3,5-dichloro-1-oxy-pyridin-4-yl)-ethyl ester |
| 58 | 3-cyclopropylmethoxy-4-difluoromethoxy-benzoic acid 1-(3-cyclopropylmethoxy-4-difluoromethoxy-phenyl)-2-(3,5-dichloro-1-oxy-pyridin-4-yl)-ethyl ester |
| 59 | 4-(3-cyclopropylmethyl-ureido)-benzoic acid 1-(3-cyclopropylmethoxy-4-difluoromethoxy-phenyl)-2-(3,5-dichloro-1-oxy-pyridin-4-yl)-ethyl ester |
| 60 | quinoline-8-carboxylic acid 1-(3-cyclopropylmethoxy-4-difluoromethoxy-phenyl)-2-(3,5-dichloro-1-oxy-pyridin-4-yl)-ethyl ester |
| 61 | 3-cyclopropylmethoxy-4-dimethylamino-benzoic acid 1-(3-cyclopropylmethoxy-4-difluoromethoxy-phenyl)-2-(3,5-dichloro-1-oxy-pyridin-4-yl)-ethyl ester |
| 62 | 4-[3-(2-methoxy-ethyl)-ureido]-benzoic acid 1-(3-cyclopropylmethoxy-4-difluoromethoxy-phenyl)-2-(3,5-dichloro-1-oxy-pyridin-4-yl)-ethyl ester |
| 63 | 1,3-dimethyl-2-oxo-2,3-dihydro-1H-benzoimidazole-5-carboxylic acid 1-(3-cyclopropylmethoxy-4-difluoromethoxy-phenyl)-2-(3,5-dichloro-1-oxy-pyridin-4-yl)-ethyl ester |
| 64 | 2-(2-fluoro-biphenyl-4-yl)-propionic acid 1-(3-cyclopropylmethoxy-4-difluoromethoxy-phenyl)-2-(3,5-dichloro-1-oxy-pyridin-4-yl)-ethyl ester |
| 65 | 3-cyclopropylmethoxy-4-difluoromethoxy-benzoic acid 1-(3-cyclopropylmethoxy-4-methoxy-phenyl)-2-(3,5-dichloro-pyridin-4-yl)-ethyl ester |
| 66 | 3-cyclopropylmethoxy-4-difluoromethoxy-benzoic acid 1-(3-cyclopropylmethoxy-4-methoxy-phenyl)-2-(3,5-dichloro-1-oxy-pyridin-4-yl)-ethyl ester |
| 67 | 2-(6-dimethylamino-naphthalen-2-yl)-propionic acid 1-(3-cyclopropylmethoxy-4-difluoromethoxy-phenyl)-2-(3,5-dichloro-1-oxy-pyridin-4-yl)-ethyl ester |
| 68 | 2-(6-dimethylamino-naphthalen-2-yl)-propionic acid 1-(3-cyclopropylmethoxy-4-difluoromethoxy-phenyl)-2-(3,5-dichloro-1-oxy-pyridin-4-yl)-ethyl ester |
| 69 | 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| 70 | 4-(3,7,12-trihydroxy-10,13-dimethyl-hexadecahydro-cyclopenta[a]phenanthren-17-yl)-pentanoic acid 1-(3-cyclopropylmethoxy-4-difluoromethoxy-phenyl)-2-(3,5-dichloro-pyridin-4-yl)-ethyl ester |
| 71 | 4-(3,7,12-trihydroxy-10,13-dimethyl-hexadecahydro-cyclopenta[a]phenanthren-17-yl)-pentanoic acid 1-(3-cyclopropylmethoxy-4-difluoromethoxy-phenyl)-2-(3,5-dichloro-1-oxy-pyridin-4-yl)-ethyl ester |
| 72 | acetic acid 1-(3-cyclopropylmethoxy-4-difluoromethoxy-phenyl)-2-(3,5-dichloro-pyridin-4-yl)-ethyl ester |

| Compound | Chemical name |
|---|---|
| 73 | phenyl-acetic acid 1-(3-cyclopropylmethoxy-4-difluoromethoxy-phenyl)-2-(3,5-dichloro-pyridin-4-yl)-ethyl ester |
| 74 | butyric acid 1-(3-cyclopropylmethoxy-4-difluoromethoxy-phenyl)-2-(3,5-dichloro-pyridin-4-yl)-ethyl ester |
| 75 | 4-phenyl-butyric acid 1-(3-cyclopropylmethoxydifluoromethoxy-phenyl)-2-(3,5-dichloro-pyridin-4-yl)-ethyl ester |
| 76 | 4-[3-(2-dimethylamino-ethyl)-ureido]-benzoic acid 1-(3-cyclopropylmethoxy-4-difluoromethoxy-phenyl)-2-(3,5-dichloro-1-oxy-pyridin-4-yl)-ethyl ester |
| 77 | 6-dimethylamino-naphthalene-2-carboxylic acid 1-(3-cyclopropylmethoxy-4-difluoromethoxy-phenyl)-2-(3,5-dichloro-1-oxy-pyridin-4-yl)-ethyl ester |
| 78 | acetoxy-phenyl-acetic acid 1-(3-cyclopropylmethoxy-4-difluoromethoxy-phenyl)-2-(3,5-dichloro-pyridin-4-yl)-ethyl ester |
| 79 | 1-(3-Methanesulfonylamino-4-methoxy-phenyl)-cyclopropanecarboxylic acid 1-(3-cyclopropylmethoxy-4-difluoromethoxy-phenyl)-2-(3,5-dichloro-1-oxy-pyridin-4-yl)-ethyl ester |
| 80 | 1-[3-(Cyclopropylmethyl-methyl-amino)-4-methoxy-phenyl]-cyclopropanecarboxylic acid 1-(3-cyclopropylmethoxy-4-difluoromethoxy-phenyl)-2-(3,5-dichloro-1-oxy-pyridin-4-yl)-ethylester |
| 81 | oxy-benzoic acid 1-(3-cyclopentyloxy-4-methoxy-phenyl)-2-(3,5-dichloro-pyridin-4-yl)-ethyl ester |
| 82 | 2,3-dihydro-benzo[1,4]dioxine-6-carboxylic acid 1-(3-cyclopropylmethoxy-4-difluoromethoxy-phenyl)-2-(3,5-dichloro-pyridin-4-yl)-ethyl ester |
| 83 | 3-cyclopropylmethoxy-4-difluoromethoxy-benzoic acid 2-(3,5-dichloro-pyridin-4-yl)-1-(2,2-difluoro-benzo[1,3]dioxol-5-yl)-ethyl ester |
| 84 | 3-cyclopropylmethoxy-4-difluoromethoxy-benzoic acid 2-(3,5-dichloro-pyridin-4-yl)-1-(2,3-dihydro-benzo[1,4]dioxin-6-yl)-ethyl ester |
| 85 | 3,4,5-triethoxy-benzoic acid 1-(3-cyclopropylmethoxy-4-difluoromethoxy-phenyl)-2-(3,5-dichloro-pyridin-4-yl)-ethyl ester |
| 86 | 4-fluoro-3-methoxy-benzoic acid 1-(3-cyclopropylmethoxy-4-difluoromethoxy-phenyl)-2-(3,5-dichloro-pyridin-4-yl)-ethyl ester |
| 87 | 1-methoxy-naphthalene-2-carboxylic acid 1-(3-cyclopropylmethoxy-4-difluoromethoxy-phenyl)-2-(3,5-dichloro-pyridin-4-yl)-ethyl ester |
| 88 | 3,4,5-trifluoro-benzoic acid 1-(3-cyclopropylmethoxy-4-difluoromethoxy-phenyl)-2-(3,5-dichloro-pyridin-4-yl)-ethyl ester |
| 89 | 2-(2-fluoro-biphenyl-4-yl)-propionic acid 1-(3-cyclopropylmethoxy-4-difluoromethoxy-phenyl)-2-(3,5-dichloro-1-oxy-pyridin-4-yl)-ethyl ester |
| 90 | 2-oxo-thiazolidine-4-carboxylic acid 1-(3-cyclopropylmethoxy-4-difluoromethoxy-phenyl)-2-(3,5-dichloro-1-oxy-pyridin-4-yl)-ethyl ester |
| 91 | 4-methyl-3,4-dihydro-2H-benzo[1,4]oxazine-7-carboxylic acid 1-(3-cyclopropylmethoxy-4-difluoromethoxy-phenyl)-2-(3,5-dichloro-pyridin-4-yl)-ethyl ester |
| 92 | 1-cyclopropylmethyl-3-methyl-2-oxo-2,3-dihydro-1H-benzoimidazole-5-carboxylic acid 1-(3-cyclopropylmethoxy-4-difluoromethoxy-phenyl)-2-(3,5-dichloro-1-oxy-pyridin-4-yl)ethyl ester |
| 93 | 1-(3',4'-dichloro-2-fluoro-biphenyl-4-yl)-cyclopropanecarboxylic acid 1-(3-cyclopropylmethoxy-4-difluoromethoxy-phenyl)-2-(3,5-dichloro-1-oxy-pyridin-4-yl)-ethyl ester |
| 94 | 2,3-dihydro-benzo[1,4]dioxine-6-carboxylic acid 1-(3-cyclopropylmethoxy-4-difluoromethoxy-phenyl)-2-(3,5-dichloro-1-oxy-pyridin-4-yl)-ethyl ester |
| 95 | 6-dimethylamino-naphthalene-2-carboxylic acid 1-(3-cyclopropylmethoxy-4-difluoromethoxy-phenyl)-2-(3,5-dichloro-pyridin-4-yl)-ethyl ester |
| 96 | 1-cyclopropylmethyl-1H-indole-5-carboxylic acid 1-(3-cyclopropylmethoxy-4-difluoromethoxy-phenyl)-2-(3,5-dichloro-1-oxy-pyridin-4-yl)-ethyl ester |
| 97 | 4,7,7-trimethyl-3-oxo-2-oxa-bicyclo[2.2.1]heptane-1-carboxylic acid 1-(3-cyclopropylmethoxy-4-difluoromethoxy-phenyl)-2-(3,5-dichloro-1-oxy-pyridin-4-yl)-ethyl ester |
| 98 | 2-benzyloxy-propionic acid 1-(3-cyclopropylmethoxy-4-difluoromethoxy-phenyl)-2-(3,5-dichloro-1-oxy-pyridin-4-yl)-ethyl ester |
| 99 | (3,4-dimethoxy-phenylsulfanyl)-acetic acid 1-(3-cyclopropylmethoxy-4-difluoromethoxy-phenyl)-2-(3,5-dichloro-1-oxy-pyridin-4-yl)-ethyl ester |
| 100 | 4-methanesulfonylamino-benzoic acid1-(3-cyclopropylmethoxy-4-difluoromethoxy-phenyl)-2-(3,5-dichloro-pyridin-4-yl)-ethyl ester |
| 101 | 4-[9-(4-ethyl-phenoxy)-nonyloxy]-benzoic acid 1-(3-cyclopropylmethoxy-4-difluoromethoxy-phenyl)-2-(3,5-dichloro-pyridin-4-yl)-ethyl ester |

Example 7

Preparation of 2-(4-amino-phenyl)-propionic acid 2-(3,5-dichloro-pyridin-4-yl)-1-(3,4-dimethoxy-phenyl)-ethyl ester (Compound 16)

Compound 10 (50 mg, 0.1 mmoles) is dissolved in dimethylformamide (DMF) (3 mL). Tin chloride (SnCl$_2$×2H$_2$O, 113 mg, 0.5 mmoles) is added and the resulting mixture is stirred at room temperature for 17 hours. The mixture is then diluted with water (15 mL) and extracted with Et$_2$O (2×30 mL). The organic phase is dried over Na$_2$SO$_4$ and the solvent is evaporated. The crude is purified by preparative HPLC to yield 10 mg of the title compound.

TABLE 5

| Compound | Structure | Analytical |
|---|---|---|
| 16 | (structure) | MS/ESI$^+$ 475-477-479 [MH]$^+$; $^1$H NMR (CDCl$_3$ calibrated at 7.26 ppm, mix of diast), δ: 8.31 and 8.47 (s*, 2H); 6.58 and 6.90 (m*, 6H); 6.76 (m*, 1H); 6.05 and 6.11 (dd*, 1H); 3.87 and 3.89 (s*, 3H); 3.72 and 3.87 (s*, 3H); 3.58 (m*, 2H); 3.18 and 3.26 (dd*, 1H); 1.33 and 1.34 (d*, 3H). |

Example 8

Preparation of 2-(4-methanesulphonylamino-phenyl)-propionic acid 2-(3,5-dichloro-pyridin-4-yl)-1-(3,4-dimethoxy-phenyl)-ethyl ester (Compound 17)

Compound 16 (26 mg, 0.05 mmoles) is dissolved in dry CH$_2$Cl$_2$ (10 mL) under nitrogen atmosphere. The solution is cooled to 0° C. and triethylamine (0.009 mL, 0.066 mmoles) and methanesulphonyl chloride (0.0052 mL, 0.06 mmoles) are added. The mixture is then allowed to react at room temperature for 17 hours. The reaction mixture is then diluted with water (15 mL) and extracted with AcOEt (2×30 mL). The organic phase is dried over Na$_2$SO$_4$ and the solvent is evaporated. The crude is purified by preparative HPLC to yield 10 mg of the title compound as a mixture of diastereoisomers.

TABLE 6

| Compound | Structure | Analytical |
|---|---|---|
| 17 | (structure) | MS/ESI$^+$ 553-555-557 [MH]$^+$; 1H NMR (CDCl$_3$ calibrated at 7.26 ppm, mix of diast) ppm 8.28 (s*, 2 H) 7.06-7.12 (m*, 4 H) 6.97 (dd*, 1 H) 6.89 (d*, 1 H) 6.87 (d*, 1 H) 6.43 (br. s., 1 H) 6.12 (dd*, 1 H) 3.90 (s*, 6 H) 3.59-3.70 (m*, 2 H) 3.19 (dd*, 1 H) 3.08 (s*, 3 H) 1.36 (d*, 3 H) and 1H NMR (300 MHz, CHLOROFORM-d) ppm 8.47 (s*, 2 H), 7.05-7.21 (m*, 4 H), 6.74-6.79 (m*, 2 H), 6.64-6.70 (m*, 1 H), 6.30-6.38 (m*, 1 H), 6.03-6.18 (m*, 1 H), 3.87 (s*, 3 H), 3.77 (s*, 3 H), 3.51-3.64 (m*, 2 H), 3.27 (dd*, 1 H), 3.02 (s*, 3 H), 1.34-1.41 (d*, 3 H) |

Example 9

Preparation of 1-(3-cyclopropylmethoxy-4-difluoromethoxy-phenyl)-2-(3,5-dichloro-1-oxy-pyridin-4-yl)-ethanol (Compound 18)

Intermediate 2b (100 mg, 0.25 mmoles) is dissolved in $CHCL_3$ (3 mL). m-Chloro perbenzoic acid (mCPBA, 80 mg, 0.46 mmoles) is added and the resulting solution is kept at 0° C. overnight. The mixture is then diluted with $CHCl_3$ (5 mL) and washed with 1N NaOH (5 ml). The organic phase is dried over $Na_2SO_4$ and the solvent is evaporated. The crude product is purified by crystallization with ethanol. The white solid is filtered and washed with petroleum ether to yield 70 mg of the title compound.

The following compounds were prepared following the same route using suitable reagents:

TABLE 7

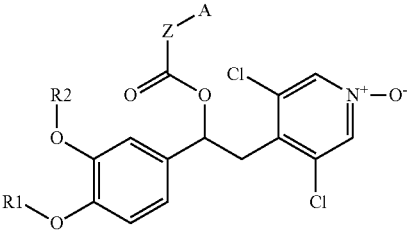

| Compound | $R_1$ | $R_2$ | Analytical |
|---|---|---|---|
| 18 | difluoromethyl | cyclopropylmethyl | MS/ESI$^+$ 420-422-424 [MH]$^+$ |
| 19 | Me | cyclopropylmethyl | MS/ESI$^+$ 384-386-388 [MH]$^+$ |
| 20 | Me | cyclopentyl | MS/ESI$^+$ 398-400-402 [MH]$^+$ |
| 21 | difluoromethyl | difluoromethyl | MS/ESI$^+$ 416-418-420 [MH]$^+$ |
| 22 | difluoromethyl | Me | MS/ESI$^+$ 380-382-384 [MH]$^+$ |
| 23 | difluoromethyl | cyclopentyl | MS/ESI$^+$ 434-436-438 [MH]$^+$ |
| 24 | Me | Me | MS/ESI$^+$ 344-346-348 [MH]$^+$ |

Example 10

Preparation of 4-(2-piperidin-1-yl-ethoxy)-benzoic acid 1-(3-cyclopropylmethoxy-4-difluoromethoxy-phenyl)-2-(3,5-dichloro-1-oxy-pyridin-4-yl)-ethyl ester hydrochloride (Compound 25)

(1-Ethyl-3-[3-dimethylaminopropyl]carbodiimide hydrochloride) (EDC.HCl) (55 mg, eq.) is added to a solution of compound 18 (60 mg, 0.14 mmol), 4-(2-piperidin-1-yl-ethoxy)-benzoic acid (81 mg, 0.28 eq.) and 4-dimethylaminopyridine (DMAP) (37 mg, 0.5 eq.) in dry DMF (4 mL) at room temperature under nitrogen atmosphere. The mixture is stirred at room temperature overnight, then it is treated with a saturated solution of $NH_4Cl$ (20 ml) and extracted with EtOAc (2×20 ml). The combined organic layers are dried over $Na_2SO_4$ and the solvent is evaporated. The crude is purified by preparative HPLC. The oily residue is dissolved in ethyl acetate (2 ml) and added with a slight excess of a 1 M solution of dry HCl in ethyl acetate. After evaporation of the solvent the residue is crystallized from methanol/diethyl ether to give 14 mg of the hydrochloride salt.

TABLE 8

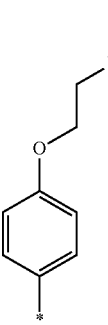

| Compound | $R_1$ | $R_2$ | Z-A | Analytical |
|---|---|---|---|---|
| 25 | $CHF_2$ | cyclopropylmethyl | | MS/ESI$^+$ 651-653-655 [MH]$^+$ 1H NMR (CD$_3$OD calibrated at 3.31 ppm) ppm 0.33-0.40 (m, 2H), 0.57-0.64 (m, 2H), 1.17-1.28 (m, 1H), 1.80-2.01 (m, 6H), 3.03-3.14 (m, 2H), 3.42-3.82 (m, 6H), 3.91-3.94 (d, 2H), 4.44-4.49 (t, 2H), 6.31-6.37 (m, 1H), 6.37-7.13 (t, 1H, CHF2), 7.08-7.17 (m, 5H), 7.99-8.05 (m, 2H), 8.42 (s, 2H). |

Legend
*NMR
s = singlet
d = doublet
t = triplet
q = quartet
dd = doublet of doublets
m = multiplet
br = broad
ESI = electrospray

Pharmacological Activity

Example 11

In Vitro Determination of PDE4 Inhibitory Activity in the Cell Free Assay

The U937 human monocytic cell line was used as source of PDE4 enzyme. Cells were cultured, harvested and supernatant fraction prepared essentially as described in Torphy, T. J. et al., *J. Pharmacol. Exp. Ther.*, 1992; 263:1195-1205. PDE4 activity was determined in cells supernatants by assaying cAMP disappearance from the incubation mixtures. 50 µl of cell supernatant were incubated at 30° C. for 30 minutes in a final volume of 200 µl in the presence of 1.6 µM cAMP with or without the test compound (50 µl).

The concentration of the test compounds ranged between $10^{-12}$ M and $10^{-6}$ M. Reactions were stopped by heat inactivation (2.5 minutes at 100° C.) and residual cAMP was measured using an electrochemiluminescence (ECL)-based immunoassay.

The results, expressed as mean±95% confidence limits of the molar concentration of the test compound producing 50% inhibition of cAMP disappearance ($IC_{50}$) are reported in Table 9 of Example 12. Percentage of inhibition of PDE4 activity was calculated, assuming cAMP disappearance in the absence of inhibitors as 100% and cAMP disappearance in heat inactivated samples as 0%. All the $IC_{50}$ values of the tested compounds, representative of the invention, were less than 0.2 microM.

Example 12

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), was performed according to a method previously described (Hatzelmann A. et al., *J. Pharmacol. Exp. Ther.*, 2001; 297:267-279; Draheim R. et al., *J. Pharmacol. Exp. Ther.*, 2004; 308:555-563. Cryopreserved human PBMCs, (100 Owen) were incubated in 96-well plates ($10^5$ cells/well), for 30 min, in the presence or absence (50 microl) of the test compounds whose concentrations ranged from $10^{-12}$ M to $10^{-6}$ M. Subsequently, LPS (3 ng/ml) was added. After 18 hours of incubation at 37° C. in a humidified incubator under an atmosphere of 95% air and 5% $CO_2$, culture medium was collected and TNF-α measured by ELISA. The results, expressed as mean±95% confidence limits of the molar concentration of the test compound producing 50% inhibition of LPS-induced TNF-a release ($IC_{50}$) are reported in Table 9.

The effects of the tested compounds were calculated as percentage of inhibition of TNF-α release, assuming LPS-induced TNF-α production in the absence of inhibitor compound as 100% and basal TNF-α production of PBMCs in the absence of LPS as 0%.

TABLE 9

In vitro PDE4 inhibition activity of representative compounds of the invention.

| Compound | IC50 cell free (nM) | IC50 PBMCS (nM) |
|---|---|---|
| 1 | 118 | 69 |
| 2 | — | 89 |
| 3 | 118 | 52 |
| 4 | 3.4 | 34.2 |
| 6 | 9 | 95 |
| 7 | 7 | 99 |
| 8 | 22 | — |
| 9 | 22 | 85 |
| 11 | 12 | 51 |
| 12 | 12 | 456 |
| 13 | 1.5 | 13 |
| 14 | 0.2 | 2 |
| 15 | 8.6 | 15 |
| 16 | 6.3 | 36 |

Example 13

Evaluation of the Ability to Inhibit the Low Affinity LPDE4 Versus the Ability to Compete for the High Affinity HPDE4

The affinity toward LPDE4 and HPDE4 was assessed as previously described respectively in Cortijo J. et al., *Br. J. Pharmacol.*, 1993, 108: 562-568 and Duplantier A. J. et al., *J. Med. Chem.*, 1996; 39: 120-125. The concentration of the test compound ranged between $10^{-12}$ M and $10^{-5}$ M. The results in terms of $IC_{50}$ are reported in Table 10. In the case of LPDE4, the $IC_{50}$ is the molar concentration of the test compound producing 50% inhibition of cAMP disappearance, while in the case of HPDE4, the $IC_{50}$ is the molar concentration of the test compound producing 50% inhibition of the binding of [$H^3$] rolipram. The results indicate that the compounds of the invention inhibited LPDE4 with subnanomolar affinity and are considerably more selective toward LPDE4 versus HPDE4.

TABLE 10

Activity profile of representative compounds of the invention

| Compound | HPDE4 $IC_{50}$ (nM) | LPDE4 $IC_{50}$ (nM) | HPDE4/ LPDE4 |
|---|---|---|---|
| 14 | 13.9 | 0.0881 | 158 |
| 15 | 2.17 | 0.169 | 273 |
| 20 | 299 | 0.759 | 394 |
| 9 | 399 | 0.738 | 541 |
| 11 | 153 | 0.116 | 1319 |

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (2):

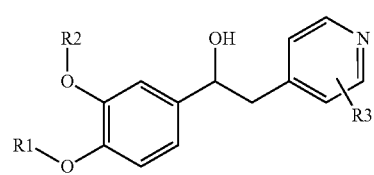

(2)

wherein:
  $R_1$ is:
    H;
    linear or branched ($C_1$-$C_6$)alkyl, optionally substituted by one or more substituents selected from ($C_3$-$C_7$) cycloalkyl and ($C_5$-$C_7$)cycloalkenyl;
    ($C_3$-$C_7$)cycloalkyl;
    ($C_5$-$C_7$)cycloalkenyl;
    linear or branched ($C_2$-$C_6$)alkenyl; or
    linear or branched ($C_2$-$C_6$)alkynyl;
  $R_2$ is cyclopropylmethyl; and
  $R_3$ is one or more substituents independently selected from the group consisting of H, CN, $NO_2$, $CF_3$ and a halogen atom,
  or an N-oxide on the pyridine ring thereof.

2. A compound or N-oxide according to claim 1, wherein $R_1$ is selected from the group consisting of methyl and difluoromethyl; and $R_3$ is two chlorine atoms on the 3- and 5-positions of the pyridine ring to which they are bonded.

3. A compound or N-oxide according to claim 1, which is an N-oxide on the pyridine ring.

4. A compound or N-oxide according to claim 1, which is not an N-oxide on the pyridine ring.

5. A compound or N-oxide according to claim 2, which is an N-oxide on the pyridine ring.

6. A compound or N-oxide according to claim 2, which is not an N-oxide on the pyridine ring.

* * * * *